United States Patent
Ebisawa

(10) Patent No.: US 10,902,635 B2
(45) Date of Patent: Jan. 26, 2021

(54) LINE-OF-SIGHT DETECTION DEVICE

(71) Applicant: NATIONAL UNIVERSITY CORPORATION SHIZUOKA UNIVERSITY, Shizuoka (JP)

(72) Inventor: Yoshinobu Ebisawa, Hamamatsu (JP)

(73) Assignee: NATIONAL UNIVERSITY CORPORATION SHIZUOKA UNIVERSITY

(*) Notice: Subject to any disclaimer, the term of this patent is extended or adjusted under 35 U.S.C. 154(b) by 62 days.

(21) Appl. No.: 16/324,583

(22) PCT Filed: Aug. 10, 2017

(86) PCT No.: PCT/JP2017/029092
§ 371 (c)(1),
(2) Date: Feb. 11, 2019

(87) PCT Pub. No.: WO2018/030515
PCT Pub. Date: Feb. 15, 2018

(65) Prior Publication Data
US 2019/0172222 A1    Jun. 6, 2019

(30) Foreign Application Priority Data
Aug. 12, 2016 (JP) .................................. 2016-158944

(51) Int. Cl.
*A61B 3/11* (2006.01)
*G06T 7/73* (2017.01)
(Continued)

(52) U.S. Cl.
CPC .............. *G06T 7/74* (2017.01); *A61B 3/113* (2013.01); *G06F 3/0346* (2013.01); *G06T 7/593* (2017.01);
(Continued)

(58) Field of Classification Search
CPC .. G06T 7/74; G06T 7/80; G06T 7/593; G06T 7/70; G06T 2207/30201; G06F 3/0346; A61B 3/113
See application file for complete search history.

(56) References Cited

U.S. PATENT DOCUMENTS

| | | | |
|---|---|---|---|
| 5,913,079 A * | 6/1999 | Aoyama .................. | G02B 7/28 396/121 |
| 8,824,779 B1 | 9/2014 | Smyth ......................... | 382/154 |

(Continued)

FOREIGN PATENT DOCUMENTS

| | | |
|---|---|---|
| JP | 2005-185431 A | 7/2005 |
| JP | 2005-230049 A | 9/2005 |

(Continued)

OTHER PUBLICATIONS

Extended European Search Report dated Dec. 10, 2019 in corresponding European Patent Application No. 17839579.4.
(Continued)

*Primary Examiner* — Gregory M Desire
(74) *Attorney, Agent, or Firm* — Ostrolenk Faber LLP

(57) ABSTRACT

A line-of-sight detection device includes a camera, a light source that causes corneal reflection, and an image processing device that obtains information on a pupil shape of an eye, a position of a pupil center, and a position of the cornea reflection and obtains a line of sight of a subject. The image processing device includes a first optical axis acquisition unit that acquires a first optical axis candidate using the position of the pupil center and the position of the cornea reflection, a second optical axis acquisition unit that obtains a second optical axis candidate using the pupil shape, an optical axis information acquisition unit that generates information for acquiring the optical axis, a calibration information unit that provides calibration information, and a visual (Continued)

axis acquisition unit that obtains a visual axis as a line of sight by calibrating an optical axis using the calibration information.

13 Claims, 21 Drawing Sheets

(51) Int. Cl.
*A61B 3/113* (2006.01)
*G06T 7/70* (2017.01)
*G06F 3/0346* (2013.01)
*G06T 7/80* (2017.01)
*G06T 7/593* (2017.01)

(52) U.S. Cl.
CPC ............. *G06T 7/70* (2017.01); *G06T 7/80* (2017.01); *G06T 2207/30201* (2013.01)

(56) References Cited

U.S. PATENT DOCUMENTS

| | | | |
|---|---|---|---|
| 9,311,527 B1* | 4/2016 | Yin | G06F 3/00 |
| 9,706,916 B2* | 7/2017 | Kersting | A61F 9/007 |
| 9,760,774 B2* | 9/2017 | Yamashita | G06K 9/2018 |
| 10,379,609 B2* | 8/2019 | Nagamatsu | G08B 21/06 |
| 2007/0279590 A1 | 12/2007 | Ebisawa | 351/208 |
| 2010/0177186 A1* | 7/2010 | Baranton | G02C 13/003 348/78 |
| 2019/0011983 A1* | 1/2019 | Yasuda | G06F 3/04842 |
| 2019/0172222 A1* | 6/2019 | Ebisawa | G06T 7/70 |

FOREIGN PATENT DOCUMENTS

| | | |
|---|---|---|
| JP | 2007-271554 A | 10/2007 |
| JP | 2016-051315 A | 4/2016 |
| WO | WO 2016/098406 A1 | 6/2016 |

OTHER PUBLICATIONS

Villanueva, A. et al.: "Evaluation of Corneal Refraction in a Model of a Gaze Tracking System", IEEE Transactions on Biomedical Engineering, IEEE Service Center, Piscataway, NJ, USA, vol. 55, No. 12, Dec. 1, 2008, pp. 2812-2822, XP011342791.

International Search Report dated Oct. 31, 2017 in the counterpart Patent Application No. PCT/JP2017/029092.

International Preliminary Report on Patentability (IPRP) dated Feb. 14, 2019 in the counterpart Patent Application No. PCT/JP2017/029092.

* cited by examiner

LINE-OF-SIGHT DETECTION DEVICE

CROSS-REFERENCE TO RELATED APPLICATIONS

The present application is a 35 U.S.C. §§ 371 national phase conversion of PCT/JP2017/029092, filed Aug. 10, 2017, which claims priority to Japanese Patent Application No. 2016-158944, filed Aug. 12, 2016, the contents of both of which are incorporated herein by reference. The PCT International Application was published in the Japanese language.

TECHNICAL FIELD

One aspect of the present invention relates to a line-of-sight detection device.

BACKGROUND ART

In recent years, a line-of-sight detection device using a light source such as a near-infrared light source and a video camera has become widespread. The line-of-sight detection device uses a detection method called a "pupil-corneal reflection method". When an angle of a line-of-sight direction of a subject with respect to the video camera changes, a positional relationship between the pupil and the corneal reflection in the image obtained by the video camera changes. In the "pupil-corneal reflection method", the line-of-sight direction is obtained using this change in positional relationship. In the "pupil-corneal reflection method", first, the subject is caused to gaze at a visual target of which the coordinates are known. As a result, in the "pupil-corneal reflection method", a relationship between a positional relationship between the pupil and the corneal reflection in the image and the angle of the line-of-sight direction is obtained. Then, in the "pupil-corneal reflection method", the line-of-sight direction is obtained using the relationship. The pupil-corneal reflection method has an advantage that accuracy of the line-of-sight detection is high.

For example, Patent Literature 1 discloses a line-of-sight detection device using a pupil-corneal reflection method. The line-of-sight detection device has two or more video cameras subjected to camera calibration (stereo calibration). Each camera includes a near infrared light source. A configuration including the camera and the near-infrared light source is simply referred to as an optical system. The line-of-sight detection device obtains an image using each camera while controlling the near-infrared light source such that the near-infrared light source is lit. The line-of-sight detection device obtains the coordinates of a pupil and the coordinates of the corneal reflection of the light source using the acquired image. The line-of-sight detection device obtains a line-of-sight direction using relative positional coordinates between these. The line-of-sight detection device can detect a highly accurate gazing point through acquisition of three-dimensional coordinates of the pupil, accurate acquisition of a distance from each camera to the pupil, and calibration of a corneal reflection-pupil center vector which changes according to a change in distance. The eye-line-of-sight detection device of Patent Literature 1 needs a three-dimensional position of the pupil. Therefore, the pupil needs to be included in a plurality of images obtained by two or more cameras. Further, the pupil and the corneal reflection need to be included in at least one image to determine a line of sight angle.

CITATION LIST

Patent Literature

[Patent Literature 1] Japanese Unexamined Patent Publication No. 2005-185431

SUMMARY OF INVENTION

Technical Problem

When a line of sight of a subject is directed in a direction greatly deviated from an optical system, there is concern that the corneal reflection which is reflected light of a light source on a cornea may be forced outside of a region of the cornea. In this case, the reflected light of the light source changes from a corneal reflection to a state called white eye reflection. The accuracy of line-of-sight detection using white eye reflection tends to be low. A line-of-sight angle range in which the corneal reflection can be obtained differs greatly among subjects. The line-of-sight angle range is equal to or greater than about 30 degrees and smaller than or equal to about 40 degrees. In short, in the pupil-corneal reflection method, the angle range in which the line-of-sight direction can be detected tends to be limited. In a line-of-sight detection device of the related art, a light source is attached to a camera. According to this configuration, when the subject looks in a direction greatly deviated with respect to a direction directed to the camera, a state in which a corneal reflection does not appear may arise. Therefore, in the pupil-corneal reflection method using corneal reflection, it is difficult to extend the range in which the line of sight can be detected.

The present invention provides a line-of-sight detection device capable of extending a detection range of a line-of-sight direction of a subject.

Solution to Problem

A line-of-sight detection device according to one aspect of the present invention includes an image acquisition unit that obtains a plurality of eye images including eyes of a subject; a light source that is disposed near the image acquisition unit and irradiates the subject with light for causing corneal reflection in the eye; and an image processing unit that acquires information on a pupil shape of the eye, a position $(P_S)$ of a pupil center and a position $(G_S)$ of corneal reflection included in the plurality of eye images using the plurality of eye images, and obtains a line of sight of the subject based on the acquired information, wherein the image processing unit includes a first optical axis acquisition unit that acquires a first optical axis candidate using the position $(P_S)$ of the pupil center and the position $(G_S)$ of the corneal reflection; a second optical axis acquisition unit that acquires a second optical axis candidate by using the pupil shape; an optical axis information acquisition unit that generates information for acquiring the optical axis using at least one of the first optical axis candidate and the second optical axis candidate on the basis of the pupil shape; a calibration information unit that provides calibration information obtained by indicating a deviation of the optical axis with respect to a visual axis of the eye according to an angle; and a visual axis acquisition unit that obtains the visual axis as the line of sight by calibrating the optical axis using the calibration information.

The line-of-sight detection device includes the first optical axis acquisition unit and the second optical axis acquisition unit. The first optical axis acquisition unit obtains the optical axis using the position ($P_S$) of the pupil center and the position ($G_S$) of the corneal reflection. Therefore, the first optical axis acquisition unit can detect the line of sight in the range of the line of sight in which the corneal reflection can be obtained. The second optical axis acquisition unit obtains the optical axis using the shape of the pupil. Therefore, the second optical axis acquisition unit can detect the line of sight even in the range of the line of sight in which the corneal reflection cannot be obtained. The optical axis information acquisition unit generates information for selecting any one of the first optical axis candidate and the second optical axis candidate using the shape of the pupil. A deviation of the optical axis selected from the first optical axis candidate and the second optical axis candidate with respect to the visual axis is calibrated in the line-of-sight acquisition unit. As a result, the visual axis as a line of sight can be obtained. Therefore, the line-of-sight detection device can extend the range in which the line of sight can be satisfactorily detected, from a narrow range in which the corneal reflection can be obtained to a wide range in which the corneal reflection cannot be obtained.

The calibration information may be a deviation angle ($\theta_0$), and the deviation angle ($\theta_0$) may be a vector indicating a deviation of the optical axis with respect to the visual axis, and may be indicated by a magnitude ($|\theta_0|$) and a slope ($\phi_0$) of the optical axis with respect to the visual axis. According to this configuration, it is possible to suitably calibrate the deviation of the optical axis with respect to the line-of-sight.

The image processing unit may include a first computation unit that obtains a first vector (OP) directed from a position ($O_S$) of the image acquisition unit to the position ($P_S$) of the pupil center; a second computation unit that obtains a second vector (r) directed from the position ($G_S$) of the corneal reflection to the position ($P_S$) of the pupil center; a third computation unit that obtains a virtual viewpoint plane having the first vector ($O_P$) as a normal; a fourth computation unit that approximates an outer shape of the pupil included in the plurality of eye images as an ellipse and obtains an ellipticity ($R=L_A/L_B$) indicated by a major diameter ($L_A$) and a minor diameter ($L_B$) of the ellipse; and a fifth computation unit that obtains a slope ($\gamma'$) between a minor axis of the ellipse and a horizontal axis, the first optical axis acquisition unit may acquire the first optical axis candidate indicated by a magnitude ($|\theta|$) of an angle ($\theta$) with reference to the first vector (OP) and a slope ($\phi$) with reference to a horizontal axis included in the virtual viewpoint plane using a magnitude ($|r|$) of the second vector (r) associated with the magnitude ($|\theta|$) of the angle ($\theta$) and a slope ($\phi'$) formed by the second vector (r) associated with the slope ($\phi$) and the horizontal axis, and the second optical axis acquisition unit may obtain the second optical axis candidate indicated by the magnitude ($|\theta|$) of the angle ($\theta$) with reference to the first vector (OP) and the slope ($\phi$) with reference to the horizontal axis included in the virtual viewpoint plane using the ellipticity (R) associated with the magnitude ($|\theta|$) of the angle ($\theta$) and the slope ($\gamma'$) associated with the slope ($\phi$).

According to this configuration, the first optical axis candidate can be suitably obtained in the first optical axis acquisition unit. Further, the second optical axis candidate can be suitably obtained in the second optical axis acquisition unit.

The first optical axis acquisition unit may associate the magnitude ($|r|$) of the second vector (r) with the magnitude ($|\theta|$) of the angle ($\theta$) using a first coefficient (k). According to the first coefficient (k), it is possible to suitably convert the magnitude ($|r|$) of the second vector (r) to the magnitude ($|\theta|$) of the angle ($\theta$).

The image acquisition unit may include a first camera that obtains a first eye image included in the plurality of eye images and that is disposed at a first camera position ($O_{S1}$), and a second camera that obtains a second eye image included in the plurality of eye images and that is disposed at a second camera position ($O_{S2}$), the eye may include a first eye and a second eye, the first eye may include a position ($G_{S1}$) of first corneal reflection, a position ($P_{S1}$) of a first pupil center, and a first optical axis, the second eye may include a position ($G_{S2}$) of second corneal reflection, a position ($P_{S2}$) of a second pupil center, and a second optical axis, the image processing unit may further include a sixth computation unit that obtains information on a first virtual optical axis plane including the first camera position ($O_{S1}$), the position ($P_{S1}$) of the first pupil center, and a position at which the first optical axis intersects a first virtual viewpoint plane having a fourth vector as a normal on the basis of a third vector ($r_1$) directed from the position ($G_{S1}$) of the first corneal reflection to the position ($P_{S1}$) of the first pupil center and the fourth vector from the first camera position ($O_{S1}$) to the position ($P_{S1}$) of the first pupil center using the first eye image; a seventh computation unit that obtains information on a second virtual optical axis plane including the second camera position ($O_{S2}$), the position ($P_{S2}$) of the second pupil center, and a position at which the second optical axis intersects a second virtual viewpoint plane having a sixth vector as a normal on the basis of a fifth vector ($r_2$) directed from the position ($G_{S2}$) of the second corneal reflection to the position ($P_{S2}$) of the second pupil center and the sixth vector from the second camera position ($O_{S2}$) to the position ($P_{S2}$) of the second pupil center using the second eye image; and a coefficient unit that obtains the first coefficient (k), and the coefficient unit may obtain the first coefficient ($k_1$) corresponding to the first eye using a fifth angle ($\theta_1$) obtained from an intersection line at which the first virtual optical axis plane and the second virtual optical axis plane intersect each other, and a magnitude ($|r_1|$) of the third vector ($r_1$), and obtain the first coefficient ($k_2$) corresponding to the second eye using a fifth angle ($\theta_2$) obtained from the intersection line and the sixth vector, and a magnitude ($|r_2|$) of the fifth vector ($r_2$).

According to this configuration, each time the image acquisition unit obtains an image, the line of sight and the first coefficient ($k_1$, $k_2$) are obtained. Therefore, it becomes possible to sequentially update the first coefficient ($k_1$, $k_2$). As a result, it is possible to improve accuracy of conversion of the magnitude ($|r|$) of the second vector (r) to the magnitude ($|\theta|$) of the angle ($\theta$). Further, even when a relationship between the magnitude ($|r|$) of the second vector (r) and the magnitude ($|\theta|$) of the angle ($\theta$) is nonlinear, it becomes possible to obtain the first coefficient ($k_1$, $k_2$) corresponding to the magnitude ($|r|$) of the second vector (r). Therefore, it is possible to further improve the accuracy of conversion of the magnitude ($|r|$) of the second vector (r) to the magnitude ($|\theta|$) of the angle ($\theta$).

The fourth computation unit may obtain a first ellipse ($R_1=L_{A1}/L_{B1}$) that is a ratio of a major diameter ($L_{A1}$) to a minor diameter ($L_{B1}$) of the ellipse indicating an outer shape of the pupil included in the first eye image using the first eye image, and obtain a second ellipse ($R2=L_{A2}/L_{B2}$) which is a ratio of a major diameter ($L_{A2}$) to a minor diameter ($L_{B2}$) of the ellipse indicating an outer shape of the pupil included in the second eye image using the second eye image, and the image processing unit may further include a direction determination unit that compares the first ellipse ($R_1$) with the second ellipse ($R_2$) to distinguish a line-of-sight direction of the subject in a horizontal direction.

According to this configuration, it is possible to obtain the line-of-sight direction through a simple process.

The second optical axis acquisition unit may associate an inverse cosine component of a reciprocal of the ellipticity (R) with the magnitude ($|\theta|$) of the angle ($\theta$) using a second coefficient (h). According to the second coefficient (h), it is possible to suitably convert the ellipticity (R) to the magnitude ($|\theta|$) of the angle ($\theta$).

The second optical axis acquisition unit may use a corrected ellipticity (R') obtained by correcting the deviation of a pupil contour caused by refraction of a cornea of an eyeball of the subject in acquisition of the magnitude ($|\theta|$) of the angle ($\theta$). According to this configuration, the deviation of the pupil contour caused by the refraction in the cornea is corrected. Therefore, it is possible to improve the accuracy of the line-of-sight detection in the pupil shape method.

The eye may include a first eye and a second eye, and the image processing unit may further include a coordinate acquisition unit that acquires respective three-dimensional coordinates of a position ($P_{S1}$) of the pupil center in the first eye, a position ($P_{S2}$) of the pupil center in the second eye, a position ($N_{S1}$) of a first nostril among a pair of nostrils of the subject, and a position ($N_{S2}$) of a second nostril among the pair of nostrils of the subject; and a face posture acquisition unit that acquires a face posture of the subject using the position ($P_{S1}$) of the pupil center, the position ($P_{S2}$) of the pupil center, the position ($N_{S1}$) of the first nostril, and the position ($N_{S2}$) of the second nostril.

According to this configuration, it is possible to extend a range in which a line of sight can be detected. Further, according to this configuration, it is possible to obtain a face posture of the subject.

The image acquisition unit may include a first camera that obtains a first image including a face of the subject, and a second camera that is disposed at a position separated from the first camera and obtains a second image including the face of the subject, and the coordinate acquisition unit may acquire the respective three-dimensional coordinates of the position ($P_{S1}$) of the pupil center in the first eye, the position ($P_{S2}$) of the pupil center in the second eye, the position ($N_{S1}$) of the first nostril, and the position ($N_{S2}$) of the second nostril using a stereo matching method based on the first image and the second image.

According to this configuration, it is possible to extend a range in which a line of sight can be detected. Further, according to this configuration, it is possible to suitably obtain a face posture of the subject.

The image acquisition unit may include one third camera that obtains a third image including a face of the subject, and the coordinate acquisition unit may include a distance computation unit that calculates a distance between three feature points generated from the first eye, the second eye, the first nostril, and the second nostril; a two-dimensional coordinate computation unit that calculates two-dimensional coordinates regarding three feature points in the third image using the third image acquired by the third camera; and a three-dimensional coordinate computation unit that calculates three-dimensional coordinates of each of the three generated feature points using the distance acquired by the distance computation unit and the two-dimensional coordinates acquired by the coordinate acquisition unit.

According to this configuration, it is possible to extend a range in which a line of sight can be detected. Further, according to this configuration, it is possible to suitably obtain a face posture of the subject.

The optical axis information acquisition unit may generate information for selecting one of the first optical axis candidate and the second optical axis candidate as the optical axis on the basis of the pupil shape. According to this configuration, it is possible to select one of the first optical axis candidate and the second optical axis candidate as the optical axis.

Advantageous Effects of Invention

According to the present invention, a line-of-sight detection device capable of extending a detection range of a line-of-sight direction of a subject can be provided.

DESCRIPTION OF EMBODIMENTS

Figure 1:
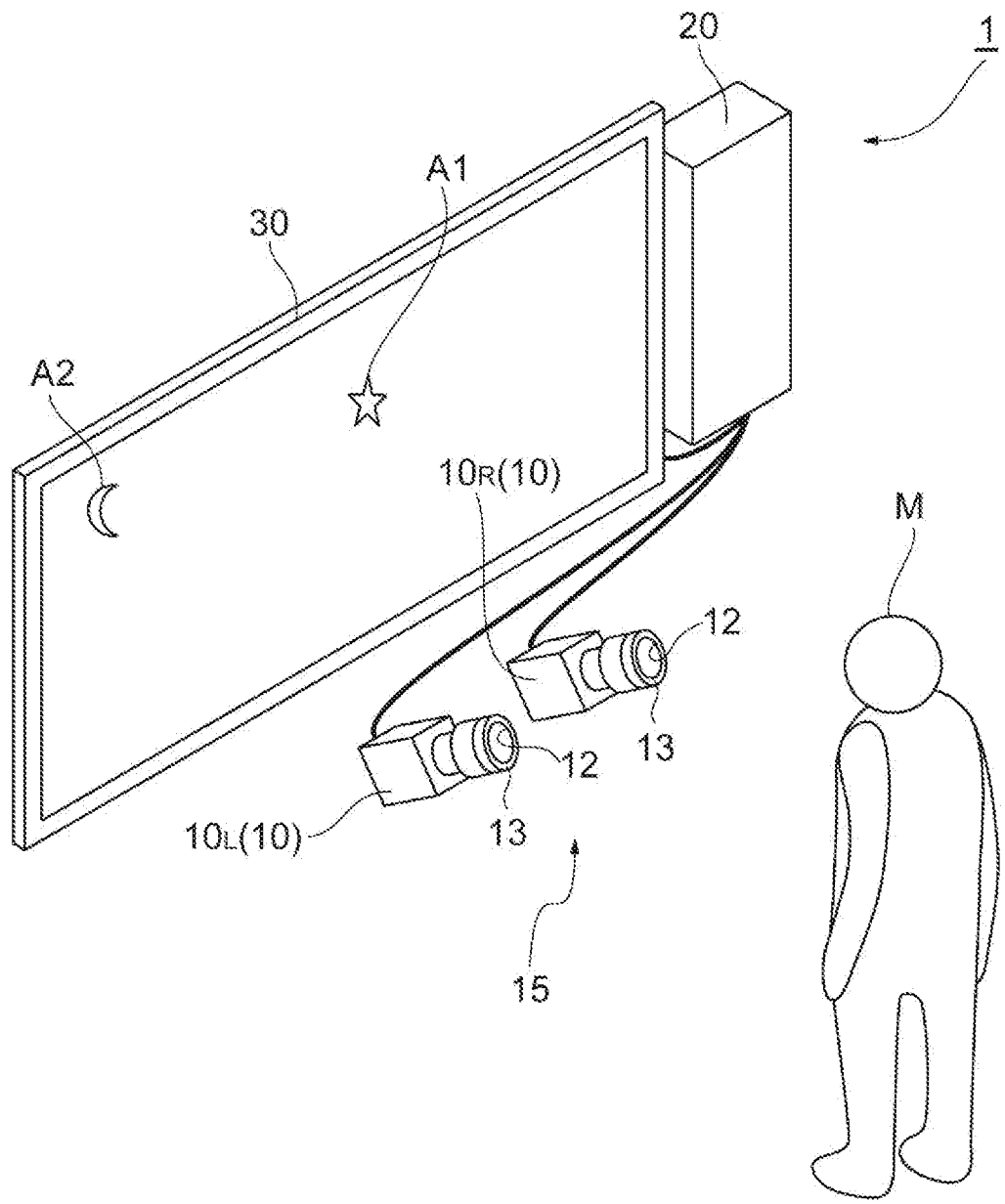
FIG. 1 is a diagram illustrating a configuration of a line-of-sight detection device according to an embodiment.

Hereinafter, modes for carrying out the present invention will be described in detail with reference to the accompanying drawings. In description of the drawings, the same elements are denoted by the same reference numerals, and duplicate description will be omitted.

As illustrated in FIG. 1, a line-of-sight detection device 1 is a computer system that detects a line-of-sight direction of a subject M viewing a display device 30. The line-of-sight detection device 1 images eyes of the subject M with an optical system 15. The optical system 15 includes a camera 10 (an image acquisition unit, a first camera, a second camera, or a third camera) and a light source 13. The line-of-sight detection device 1 detects the line-of-sight direction of the subject M using an image processing device 20 (an image processing unit). The subject M is a person who is a target of detection of the line-of-sight direction. That is, the subject M is a target person. A purpose of use of the line-of-sight detection device 1 is not limited at all. The line-of-sight detection device 1 can be used for, for example, a diagnosis device for detection of approximate driving, confirmation of a safety confirmation operation of a side mirror and a rearview mirror of a driver, detection of drowsiness of the driver, investigation of a degree of interest in a product, data input to a computer which is used for an amusement device or the like, diagnosis of autism in infants, and the like.

In the line-of-sight detection device 1, the image processing device 20 appropriately selects two line-of-sight detection processes. As a result, a range of the line of sight in which a desired accuracy can be obtained is extended. The first line-of-sight detection process is a corneal reflection-pupil center method. The corneal reflection-pupil center method is selected when the subject M is viewing a visual target A1 displayed at a position close to the camera 10. The second line of sight detection process is a pupil shape method. The pupil shape method is selected when the subject M is viewing a visual target A2 displayed at a position far from the camera 10.

Figure 2:
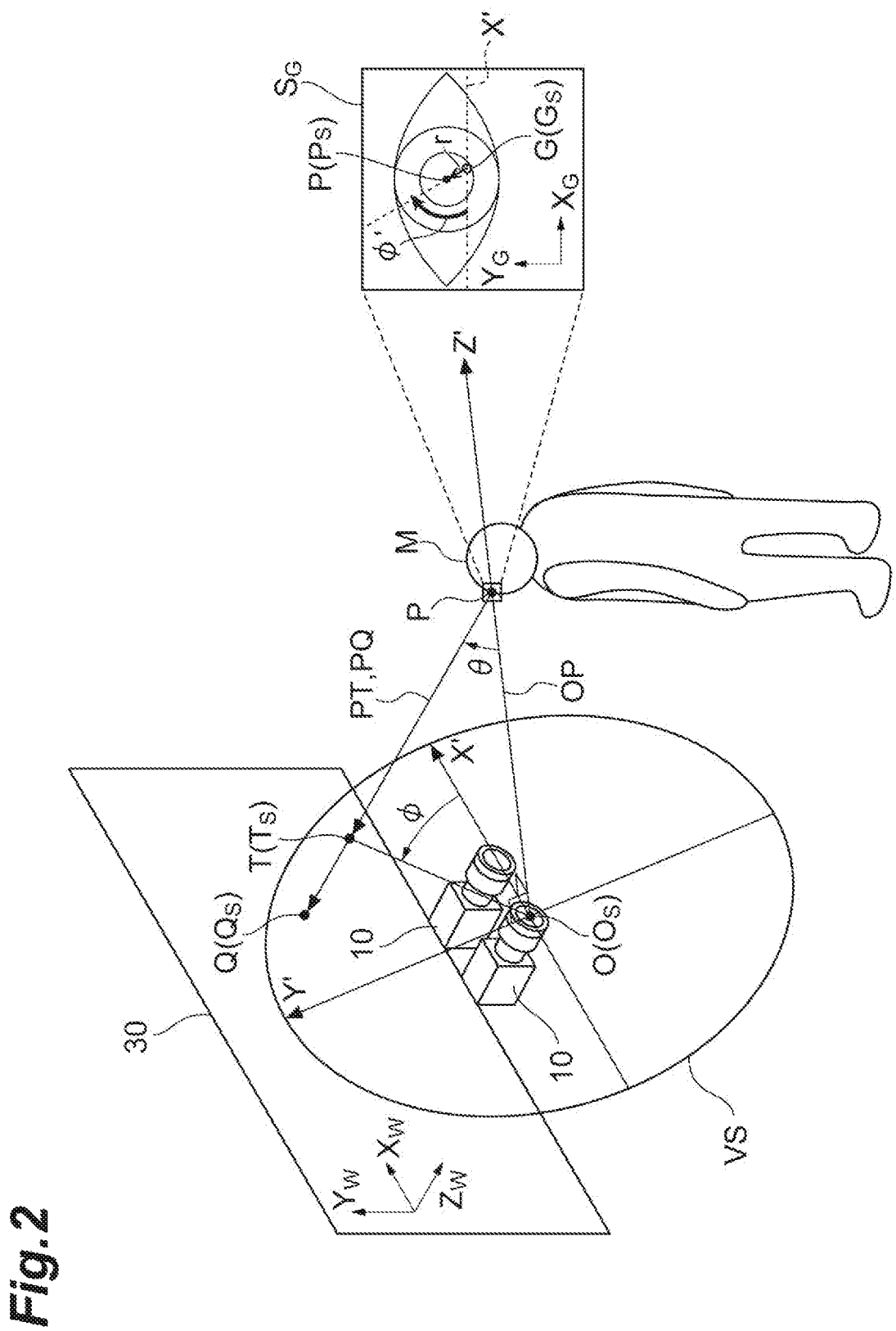
FIG. 2 is a diagram illustrating a principle of a corneal reflection-pupil center method.

As illustrated in FIG. 2, in the following description, the line of sight is a line connecting a position $P_S$ of the pupil center of the subject M to a gazing point of the subject M. The "gazing point" is a point that the subject M views. The term "line of sight" includes a meaning (concept) of a start point, an end point, and a direction. A "line-of-sight vector" indicates the line-of-sight direction of the subject M. The "line-of-sight vector" is one form expressing the "line-of-sight direction". An output destination of the line-of-sight direction which is a detection result of the image processing device 20 is not limited at all. For example, the image processing device 20 may display the determination result on a monitor with an image, a graphic, or text. Further, the image processing device 20 may store the determination result in a storage device such as a memory or a database. Further, the image processing device 20 may transmit the determination result to another computer system via a communication network.

[Corneal Reflection-Pupil Center Method]

A principle of the corneal reflection-pupil center method will be described. FIG. 2 illustrates the subject M, the camera 10, the display device 30, a virtual viewpoint plane VS, and an image example $S_G$. In the display device 30, a gazing point Q is shown. A gazing point T is shown in the virtual viewpoint plane VS. The virtual viewpoint plane VS is a virtual plane having a camera-pupil center vector OP (a first vector) to be described below as a normal. The image example $S_G$ is an example of a high-resolution image including the pupil P of the subject M. In the image example $S_G$, the pupil P and a corneal reflection G are shown.

The camera-pupil center vector OP is directed from the position $P_S$ of the pupil center to a position $O_S$ of the camera. A line-of-sight vector PQ is directed from the position $P_S$ of the pupil center to the position ($Q_S$) of the gazing point Q. The line-of-sight vector PT is directed from the position $P_S$ of the pupil center to a position $T_S$ of the gazing point T. In the corneal reflection-pupil center method, the line-of-sight vector PT is obtained as a line of sight. A corneal reflection-pupil center vector r (a second vector) shown in the image example $S_G$ is directed from a position $G_S$ of the corneal reflection to a position $P_S$ of the pupil center. In a pinhole model with an optical axis of the camera 10 as a Z axis, the corneal reflection-pupil center vector r is based on an assumption that the position $G_S$ of the corneal reflection and the position $P_S$ of the pupil center exist on a common XY plane.

The slope φ is a rotation angle around the camera-pupil center vector OP in the virtual viewpoint plane VS. The slope φ is a slope of a straight line passing through the position $O_S$ of the camera and the position $T_S$ of the gazing point T with respect to the horizontal axis X'. The slope φ is a planar angle in the virtual viewpoint plane VS. The slope φ is a scalar with magnitude |φ|. An angle θ is an angle formed by the camera-pupil center vector OP and the line-of-sight vector PQ. The angle θ is a three-dimensional angle in a three-dimensional space. The angle θ indicates one straight line (line of sight) using the magnitude |θ| and the slope φ as an argument angle. Therefore, the angle θ is indicated as θ=(|θ|, φ). A slope φ' shown in the image example $S_G$ is an angle formed by the corneal reflection-pupil center vector r and the horizontal axis X' on an image plane. The slope φ' is a planar angle on the image plane. The slope φ' is a scalar having a magnitude |φ'|.

Here, two assumptions are set for the configuration illustrated in FIG. 2.

The first assumption is shown in Equation (1). The first assumption is a relationship in which the angle θ is proportional to the corneal reflection-pupil center vector r.

[Math. 1]

$$\theta = kr \qquad (1)$$

As described above, the angle θ is indicated by the magnitude |θ| of the angle θ and the slope φ. A first coefficient k is a predetermined constant. The corneal reflection-pupil center vector r is corrected using the magnitude of the camera-pupil center vector OP. With this correction, the corneal reflection-pupil center vector r is converted to an actual magnitude. According to these definitions and Equation (1), Equation (2) is shown.

[Math. 2]

$$\theta = k|r| \qquad (2)$$

The second assumption is shown in Equation (3). The second assumption is a relationship in which the slope φ in the virtual viewpoint plane VS is equal to the slope φ' in an image including the pupil P.

[Math. 3]

$$\phi = \phi' \qquad (3)$$

(|θ|, φ) and (|r|, φ') can be caused to have a one-to-one correspondence relationship by using the first assumption and the second assumption. Therefore, the magnitude |θ| of the angle θ and the slope φ are obtained by using the corneal reflection-pupil center vector r and the slope φ'. Here, the corneal reflection-pupil center vector r is obtained from the image example $S_G$ acquired by the camera 10. According to the magnitude |θ| of the angle θ and the slope φ, the angle θ can be obtained.

It should be noted that three-dimensional coordinates of the gazing point Q in the display device 30 may be obtained using the line-of-sight vector PQ. The gazing point Q is an intersection of the line-of-sight vector PQ and the display device 30, as shown in Equation (4).

[Math. 4]

$$Q = nPT + P \quad (4)$$

[Pupil Shape Method]

Figure 3:
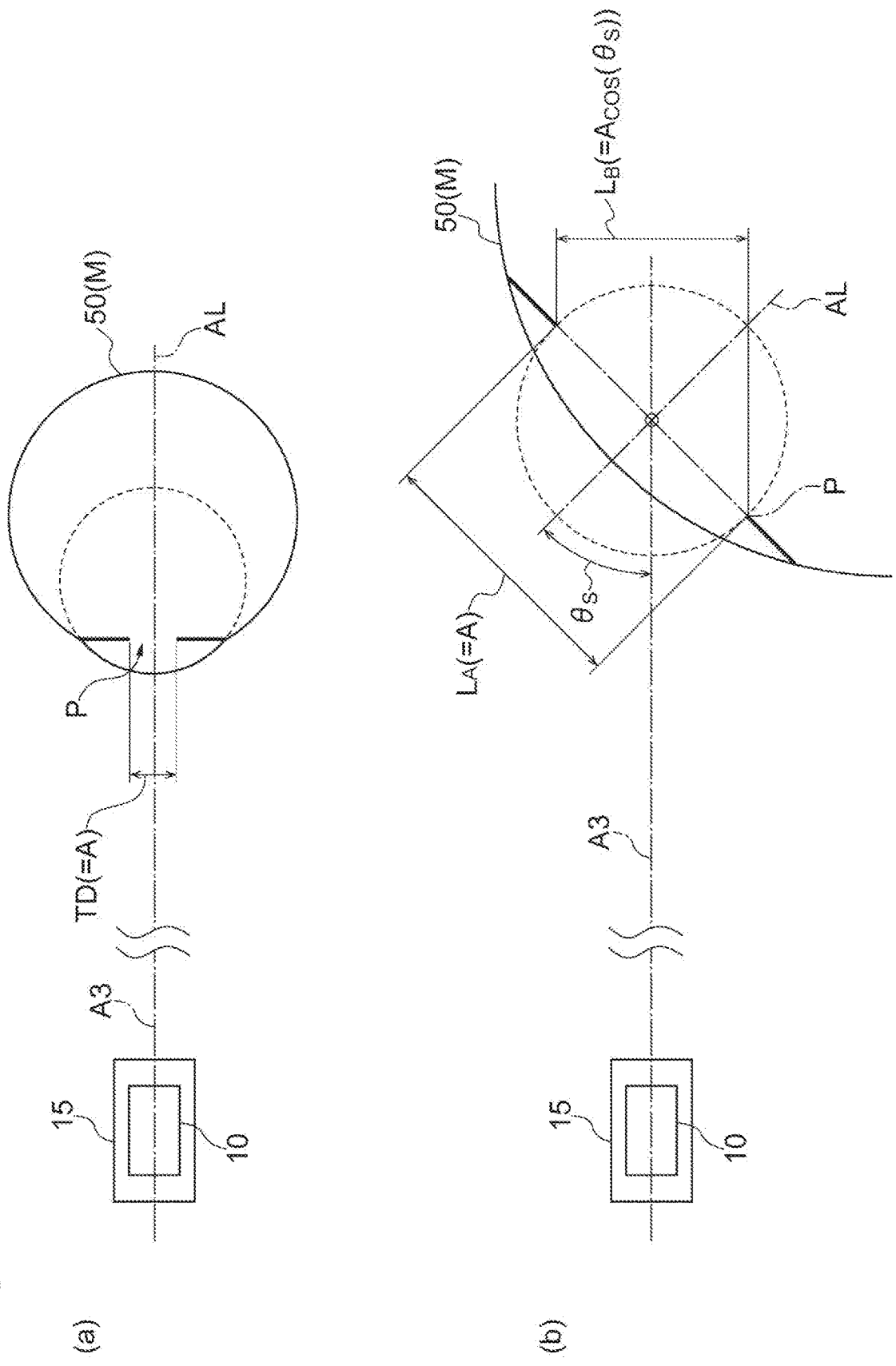
FIGS. 3(a) and 3(b) are diagrams illustrating a principle of a pupil shape method.

The pupil shape method will be described. FIG. 3(a) illustrates an eyeball 50 of the subject M when the subject M is viewing the optical system 15 including the camera 10. FIG. 3(b) illustrates the eyeball 50 of the subject M when the subject M is viewing a place different from the optical system 15. In the example illustrated in FIGS. 3(a) and 3(b), it is assumed that the eyeball 50 of the subject M is at infinity from the optical system 15 including the camera 10. As illustrated in FIG. 3(a), when the subject M is viewing the optical system 15, a shape of the pupil P in the image obtained from the camera 10 is a circle. A diameter TD of this circle is a length A. On the other hand, as illustrated in FIG. 3(b), when an optical axis AL of the eyeball 50 is tilted by the slope $\theta_S$ with respect to the axis A3, a shape of the pupil P in the image is an ellipse. This ellipse is indicated by a major diameter $L_A$ and a minor diameter LB (see Equation (5)).

[Math. 5]

$$\text{major diameter} = A$$

$$\text{minor diameter} = A \cos(\theta_S) \quad (5)$$

Here, an ellipticity R is defined. When the shape of the pupil P in the image is an ellipse, the ellipticity R is shown by the major diameter $L_A$ and the minor diameter $L_B$ (see Equation (6)).

[Math. 6]

$$\text{ellipticity} = \frac{\text{major diameter}}{\text{minor diameter}} \quad (6)$$

According to Equations (5) and (6), the slope $\theta_S$ is shown by Equation (7). This slope $\theta_S$ corresponds to the magnitude |θ| of the angle θ in FIG. 3 (a).

[Math. 7]

$$\theta_S = \cos^{-1}\left(\frac{\text{minor diameter}}{\text{major diameter}}\right) = \cos^{-1}\left(\frac{1}{\text{ellipticity}}\right) \quad (7)$$

Figure 4:
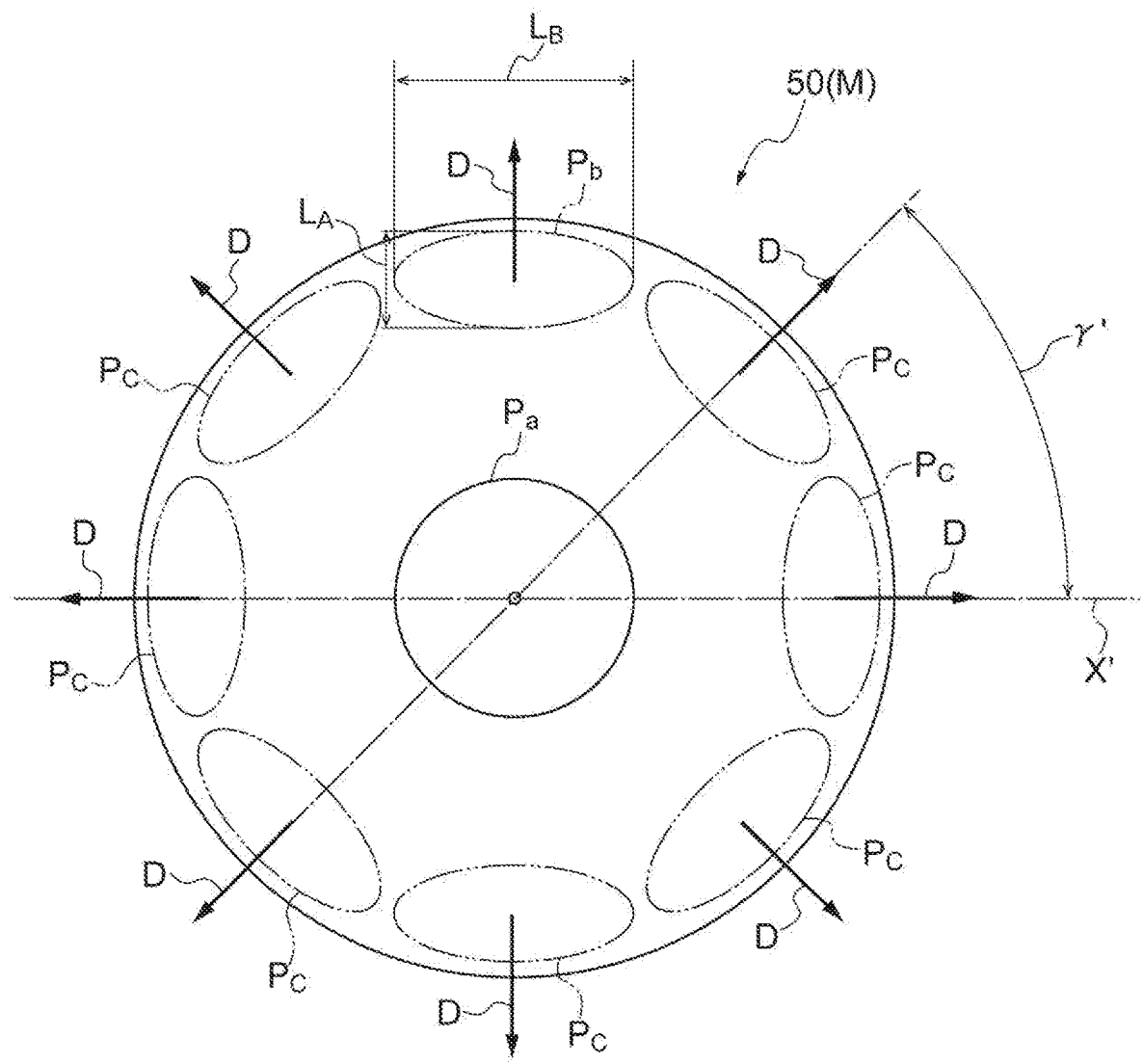
FIG. 4 is a diagram illustrating the principle of the pupil shape method.

FIG. 4 illustrates the eyeball 50 as viewed from the optical system 15. For example, a pupil Pa indicates a state when the subject M is viewing the optical system 15. A pupil Pb indicates a state when the subject M views a side above the optical system 15. Another pupil Pc indicates a state when the subject M is viewing a position different from the optical system 15. An arrow D indicates the line-of-sight direction. As illustrated in FIG. 4, a minor axis direction of an ellipse indicating the shape of the pupil P changes according to the line-of-sight direction (an arrow D). The minor axis direction is indicated by a slope γ' of the line-of-sight direction (an arrow D) with respect to the horizontal axis X'. The slope γ' corresponds to the slope φ in FIG. 2 (γ'=φ).

Therefore, the magnitude |θ| of the angle θ and the slope φ are obtained by obtaining the inverse cosine component (slope $\theta_S$) and the direction of the minor axis (slope γ'). Here, the inverse cosine component (slope $\theta_S$) is obtained from the shape of the pupil P included in the image. Accordingly, the line-of-sight vector PT indicated by the magnitude |θ| of the angle θ and the slope φ is obtained.

[Deviation Between Optical Axis and Visual Axis]

Figure 5:
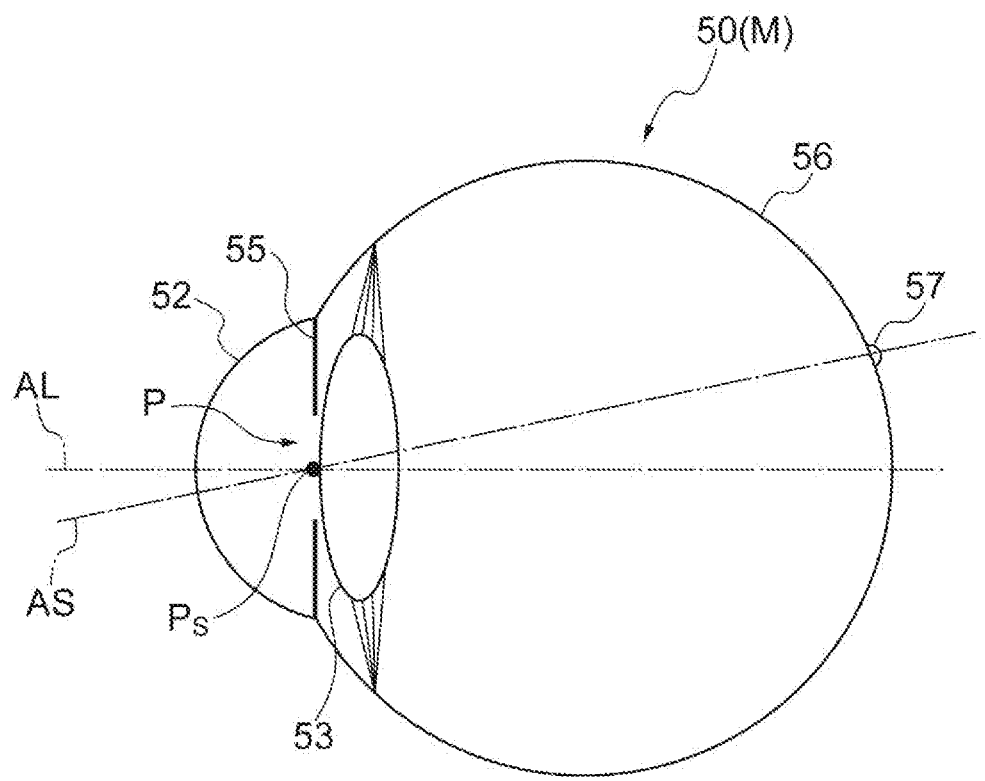
FIG. 5 is a diagram illustrating a deviation of an optical axis with respect to a visual axis.

FIG. 5 illustrates the optical axis AL and the visual axis AS in the eyeball 50. The optical axis AL is a symmetrical axis of the optical system of the eyeball 50. The visual axis AS is an axis on which the subject M actually views a visual target. The visual axis AS passes through a fovea centralis 57 in a retina 56. In general, the visual axis AS is deviated by about 5 degrees from the optical axis AL.

A result of the corneal reflection-pupil center method and the pupil shape method described above is the optical axis AL. Therefore, in the cornea reflection-pupil center method and the pupil shape method, it is assumed that the optical axis AL corresponds to the line of sight. There is a deviation between the visual axis AS and the optical axis AL. The visual axis AS is an axis passing through the position $P_S$ of the pupil center and the fovea centralis 57. The optical axis AL is a normal extending from the cornea 52 to a center of a crystalline lens 53. According to this deviation, when the subject M gazes at the optical system 15, the position $G_S$ of the corneal reflection does not match the position $P_S$ of the pupil center. Therefore, when the results obtained by the corneal reflection-pupil center method and the pupil shape method are calibrated, an output result of the line-of-sight detection device 1 approaches an actual line of sight.

[Method of Calibrating Optical Axis According to Comparative Example]

It is assumed that the optical axis AL of the eyeball 50 corresponds to the visual axis AS. In this case, in the corneal reflection-pupil center method, a relationship shown in Equation (8) is established between the corneal reflection-pupil center vector r and the angle θ formed by the camera-pupil center vector OP and the line-of-sight vector PQ. Here, the angle $\theta_L$ indicates that the angle $\theta_L$ is based on the assumption that the optical axis AL is the line of sight.

[Math. 8]

$$\theta_L = kr \quad (8)$$

Here, the deviation between the visual axis AS and the optical axis AL depends on the eyeball 50. It is assumed that a cause of the deviation is included in the corneal reflection-pupil center vector r in Equation (8). This assumption is expressed by Equation (9) below.

[Math. 9]

$$r_S = r - r_0 \quad (9)$$

In Equation (9), a deviation vector $r_0$ indicates a deviation between the visual axis AS and the optical axis AL. The deviation vector $r_0$ is obtained through gazing point calibration. The corneal reflection-pupil center vector r corresponds to the optical axis AL. The corneal reflection-pupil center vector r is obtained using the pupil P and the corneal reflection G on the image. The vector $r_S$ corresponds to the visual axis AS obtained by removing the deviation (deviation vector $r_0$) from the optical axis AL. Here, it is assumed that the corneal reflection-pupil center vector r in Equation (6) is a vector $r_S$ indicating the visual axis AS, instead of assuming that the optical axis AL of the eyeball 50 is the visual axis AS (the line of sight). According to this assumption, Equation (10) is obtained. In Equation (10), the slope $\theta_S$ indicates that the slope $\theta_S$ is based on the assumption that the visual axis AS is the line of sight.

[Math. 10]

$$\theta_S = kr_S = k(r-r_0) = kr - kr_0 \quad (10)$$

Here, the first coefficient k is a constant value. In the description of the corneal reflection-pupil center method, it is assumed that there is a linear relationship between the magnitude $|\theta|$ of the angle $\theta$ and the magnitude $|r|$ of the corneal reflection-pupil center vector r (see Equation (2)). This relationship is established when the angle $\theta$ is small. However, this relationship is not established when the angle $\theta$ is great. Therefore, the first coefficient k is changed according to the magnitude $|\theta|$ of the angle $\theta$ or the magnitude $|r|$ of the corneal reflection-pupil center vector r. That is, the relationship between the magnitude $|\theta|$ of the angle $\theta$ and the magnitude $|r|$ of the corneal reflection-pupil center vector r is assumed to be nonlinear. Then, a second term $(-k |r_0|)$ of Equation (10) caused by the deviation between the visual axis AS and the optical axis AL changes according to the first coefficient k. Therefore, the deviation (the deviation vector $r_0$) between the visual axis AS and the optical axis AL which is supposed to be unique to the eyeball 50 changes according to the magnitude $|\theta|$ of the angle $\theta$, resulting in contradiction.

[Optical Axis Calibration Method According to Embodiment]

Figure 6:
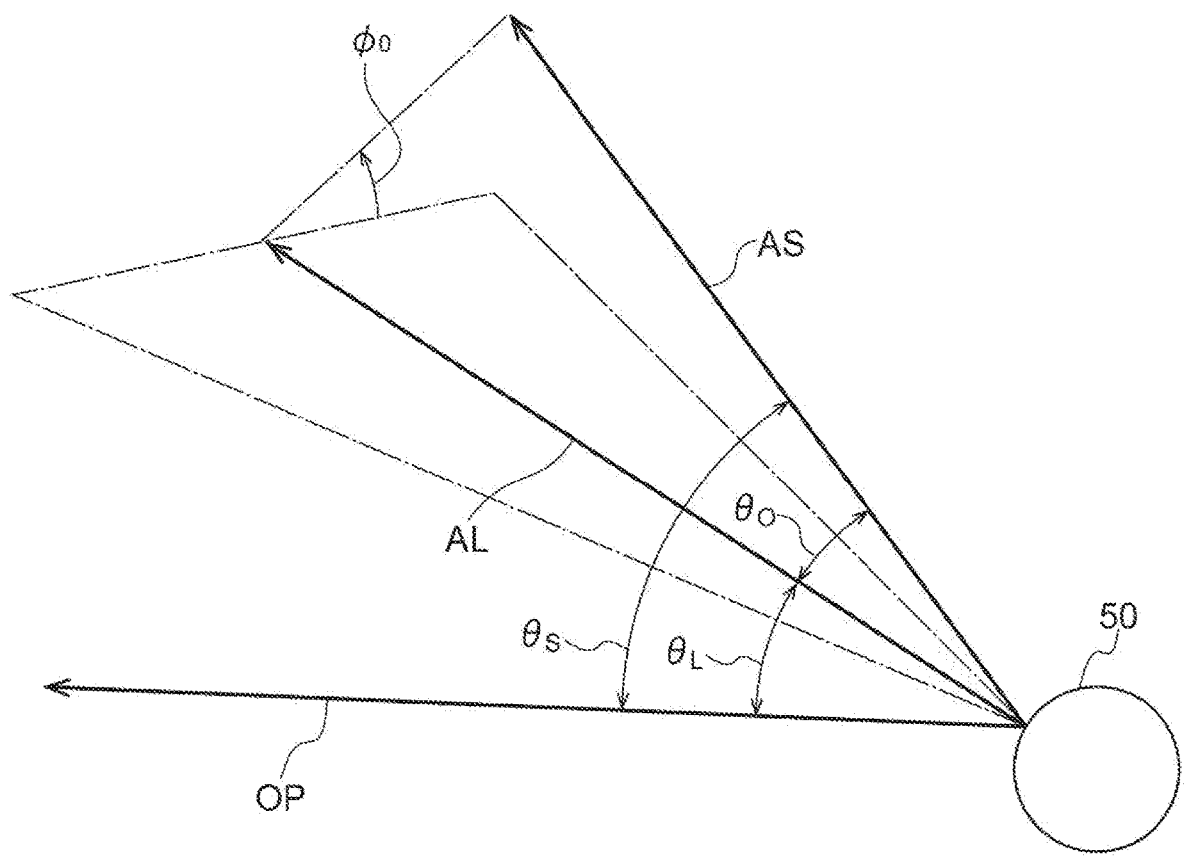
FIG. 6 is a diagram illustrating calibration of the deviation of the optical axis.

The line-of-sight detection device 1 introduces a deviation angle $\theta_0$. The deviation angle $\theta_0$ indicates a deviation of the optical axis AL with respect to the visual axis AS. As illustrated in FIG. 6, according to the deviation angle $\theta_0$, Equation (11) is obtained as a new definition equation instead of Equation (10).

[Math. 11]

$$\theta_S = kr - \theta_0$$

$$\theta_S = \theta' - \theta_0 \quad (11)$$

In Equation (11), the slope $\theta_S$ corresponds to a vector indicating the visual axis AS. The deviation angle $\theta_0$ corresponds to a vector indicating a deviation of the optical axis AL with respect to the visual axis AS. The deviation angle $\theta_0$ is defined by the magnitude $|\theta_0|$ of the deviation angle $\theta_0$ and the slope $\phi_0$. The deviation angle $\theta_0$ is $\theta_0 = (|\theta_0|, \phi_0)$. According to Equation (11), no contradiction arises in the calibration method according to the comparative example. Further, Equation (11) can be applied to the corneal reflection-pupil center method. Further, Equation (11) can be applied to the pupil shape method.

[Configuration of Line-of-Sight Detection Device]

Hereinafter, a configuration of the line-of-sight detection device 1 will be described in detail. Thereafter, an operation of the line-of-sight detection device 1 will be described in detail.

As illustrated in FIG. 1, the line-of-sight detection device 1 includes a pair of cameras (the first camera and the second camera) 10 and the image processing device 20. The pair of cameras 10 are stereo cameras. The line-of-sight detection device 1 may further include the display device 30 that is a target that the subject M views. However, a purpose of use of the line-of-sight detection device 1 is not limited as already described. Therefore, an object at an end of the line of sight of the subject M is not limited to the display device 30. For example, the object at the end of the line of sight of the subject M may be a windshield of a car. In short, the display device 30 is not an indispensable element in the line-of-sight detection device 1.

The camera 10 images the eyes of the subject M. The eye of the subject M includes the pupil P and the periphery of the pupil P. The camera 10 images the subject M in response to a command from the image processing device 20. The camera 10 outputs the image to the image processing device 20. Camera calibration is performed on the camera 10 in advance. In the following description, a pair of cameras 10 are distinguished as a camera $10_L$ and a camera $10_R$, as necessary. The camera $10_L$ is disposed on the left side of the subject M. The camera $10_R$ is disposed on the right side of the subject M. The pair of cameras $10_L$ and $10_R$ are connected to the image processing device 20 wirelessly or by wire. As a result, various pieces of data or commands are transmitted and received between the camera 10 and the image processing device 20. The pair of cameras $10_L$ and $10_R$ are disposed with a predetermined interval in a horizontal direction. The pair of cameras $10_L$ and $10_R$ are disposed at positions lower than a face of the subject M. As a result, when the subject M is wearing glasses, reflected light can be prevent from being reflected in a face image that may be generated. An elevation angle of the camera 10 with respect to the horizontal axis is, for example, equal to or greater than 20 degrees and smaller than or equal to 35 degrees. According to this range, the pupil P can be reliably detected. Further, according to this range, it is possible to avoid interference with the field of view of the subject M.

The camera 10 adopts an NTSC system, which is one of interlaced scanning systems. According to the NTSC system, 30 images can be obtained per second. The image includes an odd field including odd horizontal pixel lines and an even field including even horizontal pixel lines. The image is generated by the image of the odd field and the image of the even field being alternately captured at intervals of 1/60 second. Therefore, one frame corresponds to a pair of odd field and even field.

Figure 7:
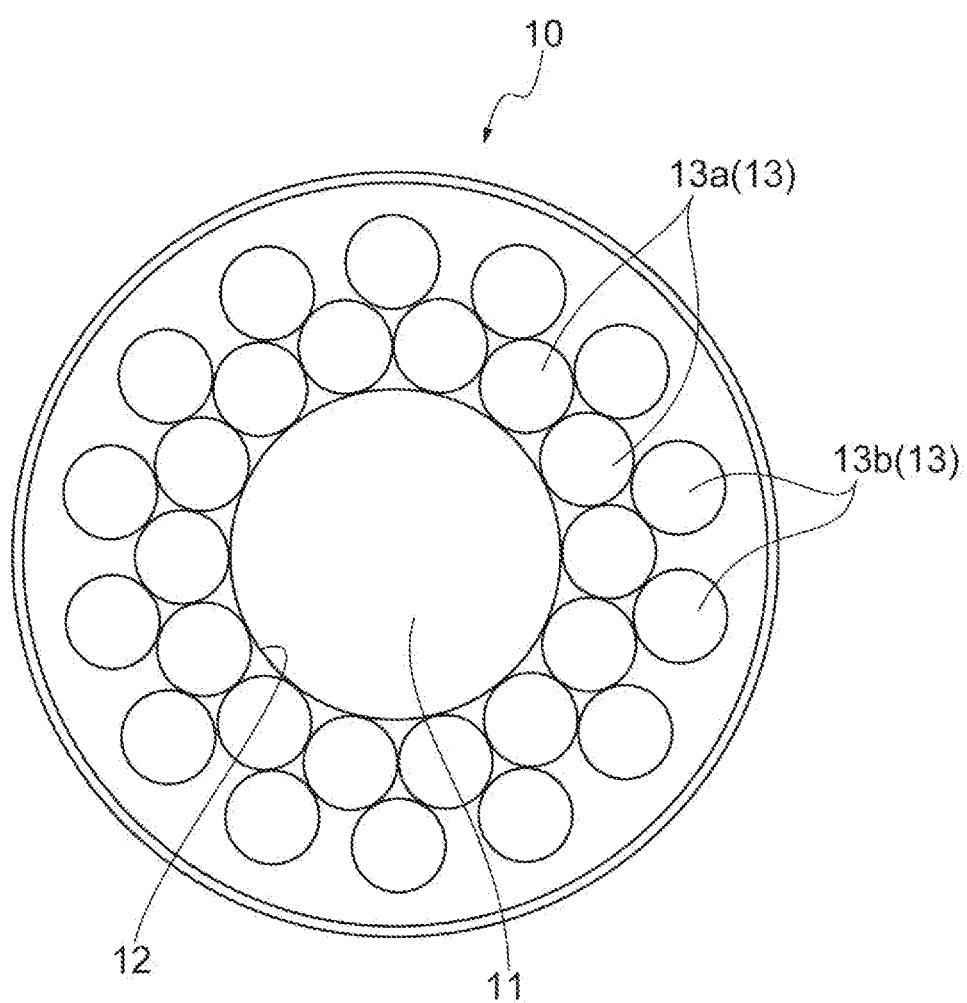
FIG. 7 is a diagram illustrating an optical system of the line-of-sight detection device.

As illustrated in FIG. 7, the camera 10 includes an objective lens 11 and a light source 13. The objective lens 11 is accommodated in a circular opening 12. The light source 13 is provided outside the opening 12. The light source 13 irradiates the eye of the subject M with illumination light. The light source 13 includes a plurality of light emitting elements 13a and a plurality of light emitting elements 13b. The light emitting elements 13a are semiconductor light emitting elements (LEDs) that emit output light having a center wavelength of 850 nm. The light emitting elements 13a are disposed in a ring shape at regular intervals along an edge of the opening 12. The light emitting elements 13b are semiconductor light emitting elements that emit output light having a center wavelength of 940 nm. The light emitting elements 13b are disposed in a ring shape at regular intervals outside the light emitting elements 13a. The light emitting elements 13a and 13b emit illumination light along the optical axis of the camera 10. It should be noted that the arrangement of the light source 13 is not limited to the configuration illustrated in FIG. 7, and other arrangements may be adopted as long as the camera 10 can be regarded as a pinhole model. The light source 13 emits illumination light according to a timing according to a command from the image processing device 20.

The image processing device 20 controls operations of the camera 10 and the light source 13. Further, the image processing device 20 executes a process of detecting the line-of-sight direction of the subject M. The image processing device 20 may be constituted by a stationary or portable personal computer. Further, the image processing device 20 may be constituted by a workstation. Further, the image processing device 20 may be constituted by another type of computer. Alternatively, the image processing device 20 may be constituted by combining a plurality of any types of computers. When a plurality of computers are used, these computers are connected to one another via a communication network such as the Internet or an intranet.

Figure 8:
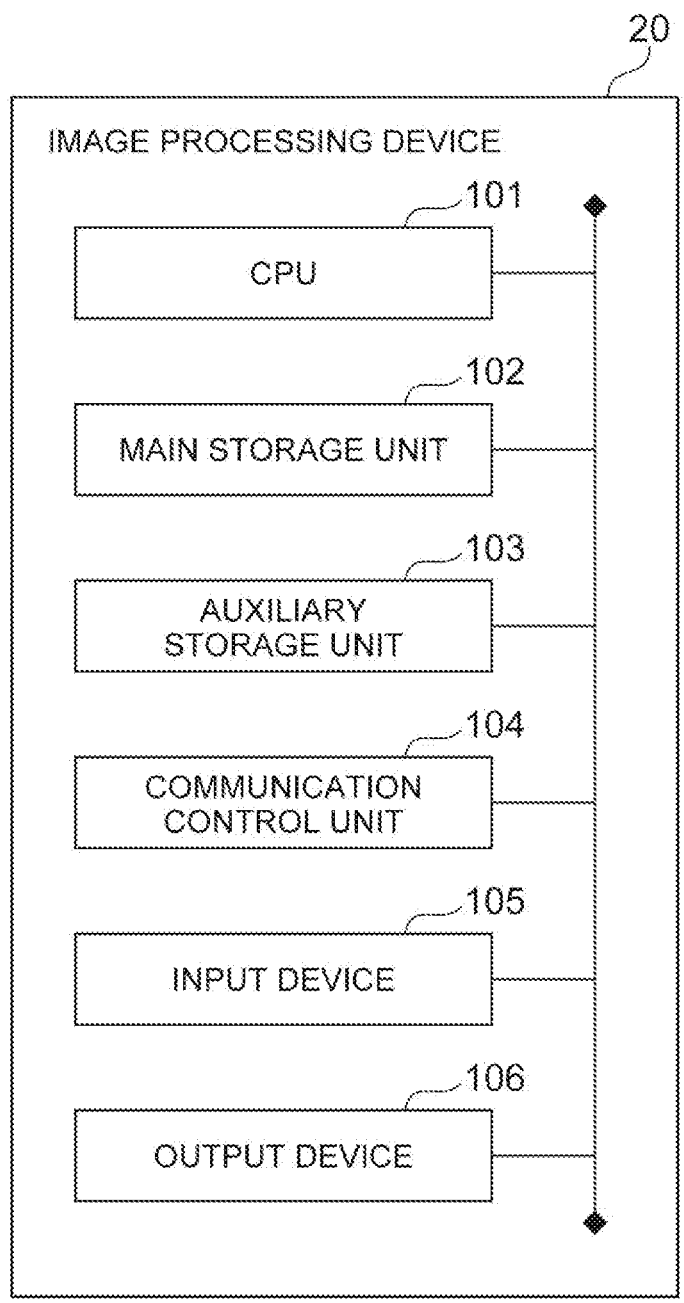
FIG. 8 is a diagram illustrating a configuration of an image processing device.

FIG. 8 illustrates a general hardware configuration of the image processing device 20. As illustrated in FIG. 8, the image processing device 20 includes a CPU (a processor) 101, a main storage unit 102, an auxiliary storage unit 103, a communication control unit 104, an input device 105, and an output device 106. The CPU 101 executes an operating system, an application program, and the like. The main storage unit 102 includes a ROM and a RAM. The auxiliary storage unit 103 includes a hard disk, a flash memory, and the like. The communication control unit 104 is constituted by a network card or a wireless communication module. The input device 105 includes a keyboard, a mouse, and the like. The output device 106 includes a display, a printer, and the like.

[Image Processing Device]

Each functional element of the image processing device 20 is realized by the following operation. The CPU 101 or the main storage unit 102 reads predetermined software. The CPU 101 operates the communication control unit 104, the input device 105, the output device 106, and the like. The main storage unit 102 or the auxiliary storage unit 103 reads and writes data. It should be noted that data or database necessary for processing is stored in the main storage unit 102 or the auxiliary storage unit 103.

Figure 9:
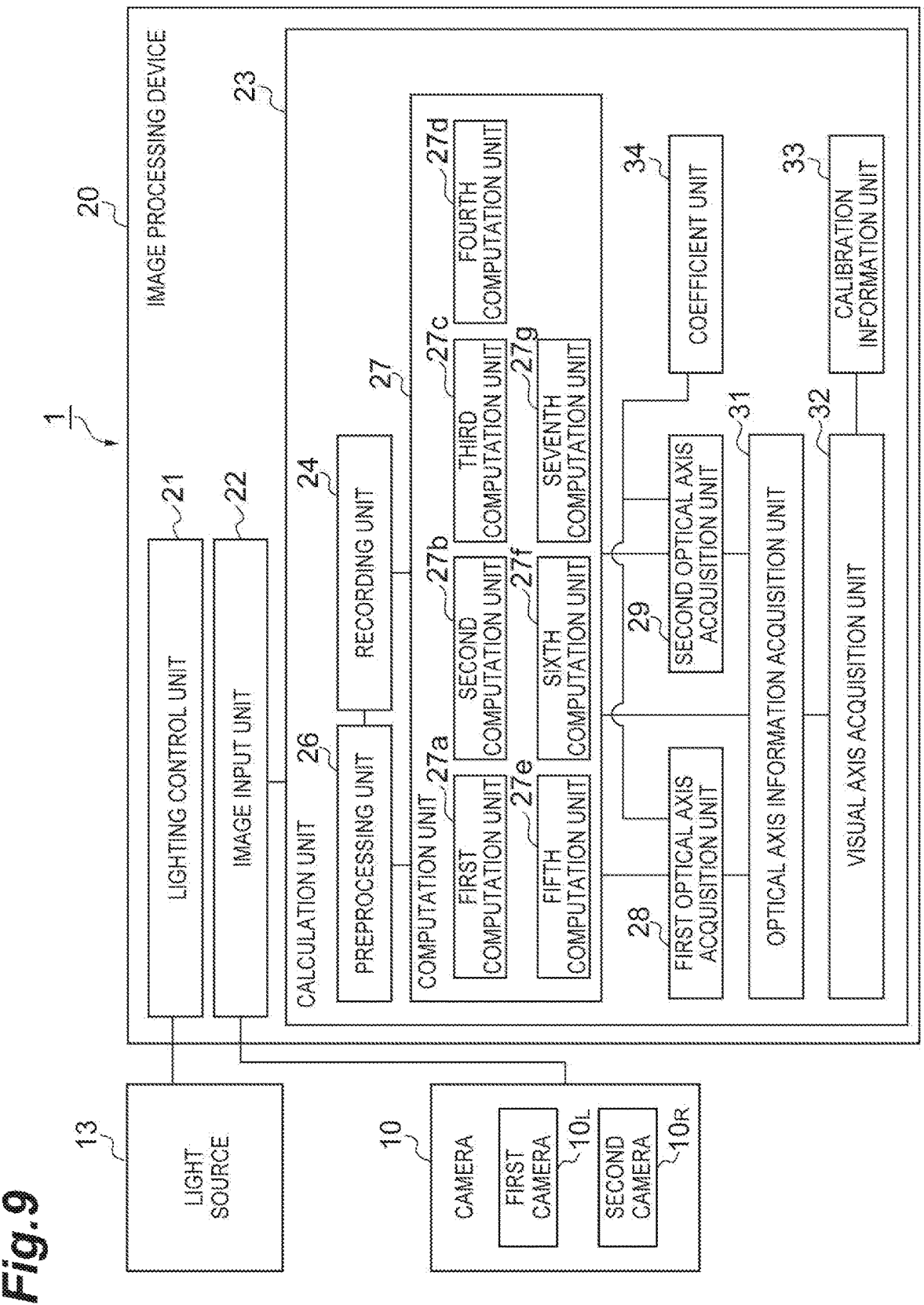
FIG. 9 is a functional block diagram illustrating a configuration of the line-of-sight detection device.

As illustrated in FIG. 9, the image processing device 20 includes a lighting control unit 21, an image input unit 22, and a calculation unit 23. The lighting control unit 21 controls a lighting timing of the light source 13. The image input unit 22 controls an imaging timing of the camera 10 in synchronization with a lighting timing of the light source 13. As a result, the image processing device 20 obtains an image (data of a plurality of eye images) from the camera 10. The calculation unit 23 detects the line of sight of the subject M by using the image input from the image input unit 22.

The calculation unit 23 includes, as functional components, a recording unit 24, a preprocessing unit 26, a computation unit 27, a first optical axis acquisition unit 28, a second optical axis acquisition unit 29, an optical axis information acquisition unit 31, a visual axis acquisition unit 32, a calibration information unit 33, and a coefficient unit 34.

The recording unit 24 has various types of information to be used for a line-of-sight detection process. The recording unit 24 can refer to from the preprocessing unit 26 and the computation unit 27. The recording unit 24 has, for example, information that is acquired in advance, such as internal parameters regarding the camera 10 or the position $O_S$ of the camera.

The preprocessing unit 26 receives information from the image input unit 22 and the recording unit 24. The preprocessing unit 26 outputs a result to the computation unit 27. Specifically, the preprocessing unit 26 receives an image from the image input unit 22. Then, the preprocessing unit 26 obtains a dark pupil image and a bright pupil image from such an image. In addition, the preprocessing unit 26 receives information on the camera 10 from the recording unit 24. Using such information, the preprocessing unit 26 obtains the position $P_S$ of the pupil center, the position $G_S$ of the cornea reflection, the long axis of the pupil P, and the minor axis of the pupil P. The preprocessing unit 26 outputs information including the position $P_S$ of the pupil center, the position $G_S$ of the cornea reflection, the long axis of the pupil P, and the minor axis of the pupil P to the computation unit 27.

The computation unit 27 receives information from the preprocessing unit 26 and the recording unit 24. The computation unit 27 outputs a result to the optical axis information acquisition unit 31, the first optical axis acquisition unit 28, and the second optical axis acquisition unit 29. Specifically, the computation unit 27 receives information including the position $P_S$ of the pupil center, the position $G_S$ of the corneal reflection, the long diameter $L_A$ of the pupil P, and the minor diameter $L_B$ of the pupil P from the preprocessing unit 26. In addition, the computation unit 27 receives information on the camera 10 from the recording unit 24. Using these pieces of information, the computation unit 27 obtains various types of information to be used for the line-of-sight detection process. The computation unit 27 includes a first computation unit 27a, a second computation unit 27b, a third computation unit 27c, a fourth computation unit 27d, a fifth computation unit 27e, and a sixth computation unit 27f.

The first computation unit 27a obtains the camera-pupil center vector OP (a first vector). The camera-pupil center vector OP is directed from the position $O_S$ of the camera to the position $P_S$ of the pupil center. The second computation unit 27b obtains the corneal reflection-pupil center vector r (a second vector). The corneal reflection-pupil center vector r is directed from the position $G_S$ of the corneal reflection to the position $P_S$ of the pupil center. The third computation unit 27c obtains the virtual viewpoint plane VS. The virtual viewpoint plane VS is a virtual plane having the camera-pupil center vector OP as a normal. The fourth computation unit 27d approximates an outer shape of the pupil P as an ellipse. As a result, the fourth computation unit 27d obtains the ellipticity R. The ellipticity R is a ratio of a major diameter to a minor axis of the ellipse. The fifth computation unit 27e obtains a gradient γ' between the minor axis of the ellipse indicating the pupil and the horizontal axis. The sixth computation unit 27f obtains information on the first virtual optical axis plane using the first eye image. Information on the first virtual optical axis plane is based on a third vector directed from the position $G_S$ of the first corneal reflection to the position $P_S$ of the first pupil center and a fourth vector directed from the first camera position to the position $P_S$ of the first pupil center. The information on the first virtual optical axis plane includes a first camera position, the position $P_S$ of the first pupil center, and a position at which a first optical axis AL1 intersects a first virtual viewpoint plane having the fourth vector as a normal. The seventh computation unit 27g obtains information on the second virtual optical axis plane using the second eye image. Information on the second virtual optical axis plane is based on a fifth vector directed from the position $G_S$ of the second corneal reflection to the position $P_S$ of the second pupil center and a sixth vector directed from the second camera position to the position $P_S$ of the second pupil center. The information on the second virtual optical axis plane includes the second camera position, the position $P_S$ of the second pupil center, and a position at which a second optical axis AL2 intersects the second virtual optical axis plane having the sixth vector as a normal.

The first optical axis acquisition unit 28 obtains the optical axis AL through a process based on the cornea reflection-pupil center method. The first optical axis acquisition unit 28 receives information from the computation unit 27. The first optical axis acquisition unit 28 outputs a result to the optical axis information acquisition unit 31. The first optical axis acquisition unit 28 obtains the optical axis AL using the position $P_S$ of the pupil center obtained from the image and the position $G_S$ of the cornea reflection. More specifically, the first optical axis acquisition unit 28 obtains the optical axis AL using the magnitude |r| of the corneal reflection-pupil center vector r (the second vector) and the slope φ' formed by the corneal reflection-pupil center vector r and the horizontal axis X'. The optical axis AL is indicated by an angle θ (first angle) with reference to the camera-pupil center vector OP and a slope φ (the second angle) with reference to the horizontal axis X' included in the virtual viewpoint plane VS. The magnitude |r| of the corneal Reflection—the pupil center vector r (the second vector) is associated with the angle θ. The corneal reflection-pupil center vector r is associated with the slope φ.

The second optical axis acquisition unit 29 obtains the optical axis AL through a process based on the pupil shape method. The second optical axis acquisition unit 29 receives information from the computation unit 27. The second optical axis acquisition unit 29 outputs a processing result to the optical axis information acquisition unit 31. The second optical axis acquisition unit 29 obtains the ellipticity R and the slope γ' (a fourth angle). The slope γ' is a slope between the minor axis and the horizontal axis X'. The second optical axis acquisition unit 29 obtains the optical axis AL using the ellipticity R associated with the angle θ and the slope γ' associated with the slope φ.

The optical axis information acquisition unit 31 receives information from the computation unit 27, the first optical axis acquisition unit 28, and the second optical axis acquisition unit 29. The optical axis information acquisition unit 31 outputs the result to the visual axis acquisition unit 32. The optical axis information acquisition unit 31 generates information for obtaining the optical axis AL using at least one of the first optical axis candidate and the second optical axis candidate on the basis of the pupil shape. The information for obtaining the optical axis AL is information for selecting one of the first optical axis candidate and the second optical axis candidate as the optical axis AL. Specifically, the optical axis information acquisition unit 31 selects any one of the first optical axis candidate and the second optical axis candidate using the shape of the pupil P obtained from the image. The optical axis information acquisition unit 31 outputs the selected optical axis candidate to the visual axis acquisition unit 32. In such a process, optical axis candidates are obtained in the first optical axis acquisition unit 28 and the second optical axis acquisition unit 29. Thereafter, an appropriate candidate is selected as a final result according to a slope of the visual axis. For example, the optical axis information acquisition unit 31 selects the first optical axis candidate when the angle θ with respect to the camera-pupil center vector OP is equal to or smaller than 30 degrees. The optical axis information acquisition unit 31 selects the second optical axis candidate when the angle θ with respect to the camera-pupil center vector OP is greater than 30 degrees. The threshold value of the angle θ may be set to a desired value.

The visual axis acquisition unit 32 receives information from the first optical axis acquisition unit 28 or the second optical axis acquisition unit 29. The visual axis acquisition unit 32 also receives information from the calibration information unit 33. The visual axis acquisition unit 32 calibrates the optical axis AL input from the first optical axis acquisition unit 28 or the second optical axis acquisition unit 29 using the calibration information. As a result, the visual axis acquisition unit 32 obtains the visual axis AS.

The calibration information unit 33 provides calibration information to the visual axis acquisition unit 32. The calibration information is the deviation angle $θ_0$ described above. The calibration information may be obtained in advance and recorded in the calibration information unit 33. The calibration information may be calculated in the calibration information unit 33. When the calibration information unit 33 obtains the calibration information, the calibration information unit 33 is connected to the computation unit 27, the first optical axis acquisition unit 28, the second optical axis acquisition unit 29, and the like. The calibration information unit 33 obtains the calibration information using the information input from such functional elements.

The coefficient unit 34 provides the first coefficient k to the first optical axis acquisition unit 28. This first coefficient k may be acquired in advance and recorded in the coefficient unit 34. Further, the first coefficient k may be calculated in the coefficient unit 34. When the coefficient unit 34 obtains the first coefficient k, the coefficient unit 34 is connected to the computation unit 27, the first optical axis acquisition unit 28, the second optical axis acquisition unit 29, and the like. The coefficient unit 34 obtains the first coefficient k using the information input from these functional components.

[Line-of-Sight Detection Process]

Next, an operation of the line-of-sight detection device 1 will be described with reference to FIG. 10.

[Overview of Process]

Figure 10:
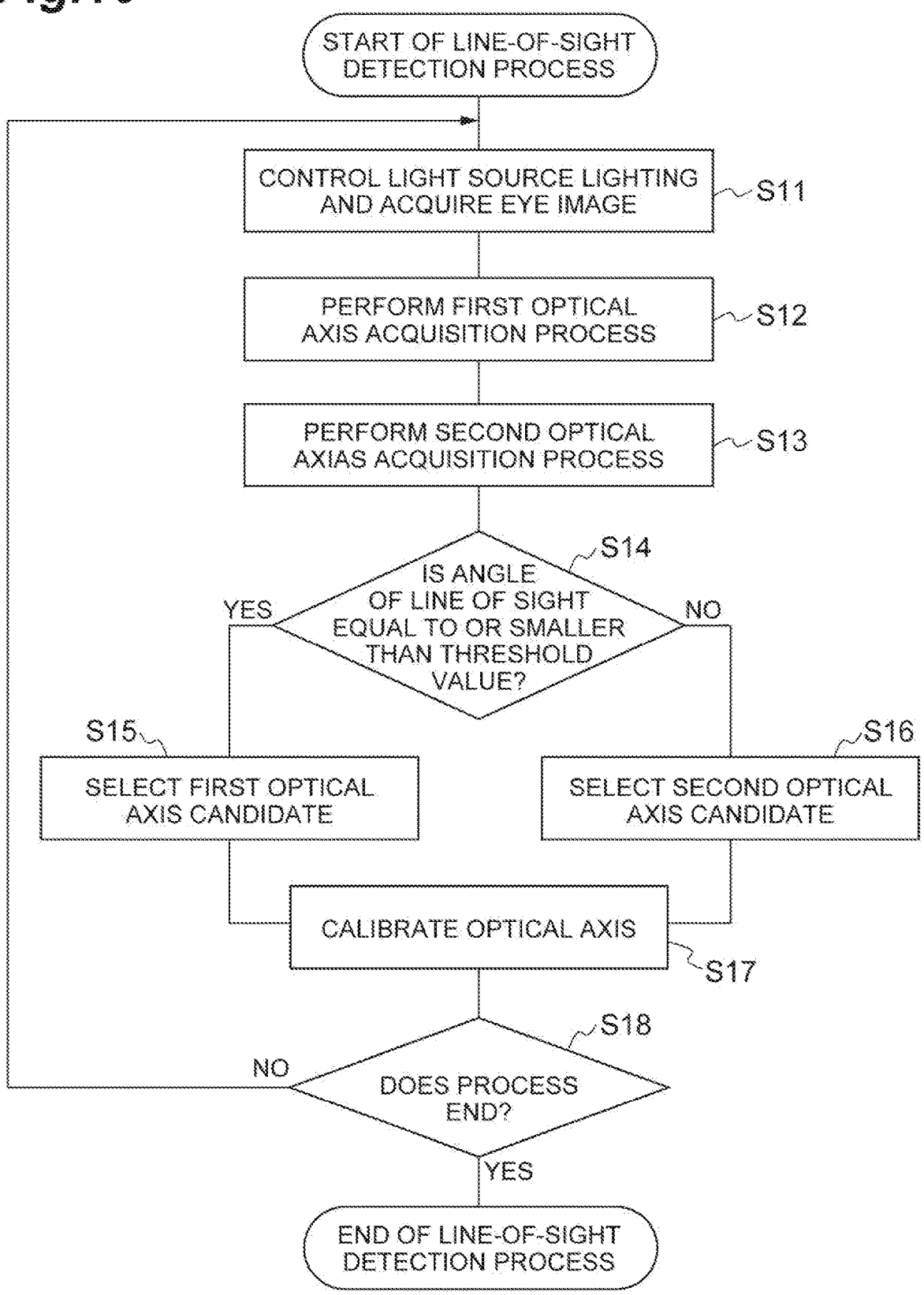
FIG. 10 is a flowchart illustrating an operation of the line-of-sight detection device.

As illustrated in FIG. 10, the lighting control unit 21 controls a lighting timing of the light source 13. The image input unit 22 acquires a bright pupil image (an eye image) and a dark pupil image (an eye image) from the respective cameras 10 in synchronization with the lighting timing (step S11). Subsequently, the first optical axis acquisition unit 28 obtains the first optical axis candidate (step S12). Subsequently, the second optical axis acquisition unit 29 obtains the second optical axis candidate (step S13). Subsequently, the optical axis information acquisition unit 31 determines which of results of the corneal reflection-pupil center method and the pupil shape method as the line-of-sight detection processes is selected as an output using the shape of the pupil P (steps S14, S15, and S16). Subsequently, the visual axis acquisition unit 32 calibrate the optical axis candidate using the calibration information (step S17). The visual axis AS is obtained as a line of sight by executing steps S11, S12, S13, S14, S15, S16, and S17. Subsequently, the calculation unit 23 determines whether or not the process of obtaining the line of sight ends (step S18). When it is determined that the process ends, the image processing device 20 ends the line-of-sight detection process (step S18: YES). When it is determined that the process does not end, the image processing device 20 executes the respective steps sequentially from step S11 again. The above process is repeatedly executed until an instruction to end the line-of-sight detection process is received.

Hereinafter, the process of each step will be described in detail.

[Acquisition of Eye Image]

Light incident on the eye is diffusely reflected by the retina. Among the diffusely reflected light, the light passing through the pupil P has a property of returning to the light source with strong directivity. When exposure of the camera and light emission of the light source disposed near an opening of the camera are performed at the same time, a part of the light reflected by the retina is incident on the opening 12 of the camera 10. Therefore, according to the optical system 15, it is possible to obtain the bright pupil image. In the bright pupil image, the pupil P appears brighter than the periphery of the pupil P. On the other hand, when the exposure of the camera 10 and the light emission of the light source 13 disposed at a position apart from the opening 12 of the camera 10 are performed at the same time, the light returning from the eye does not substantially return to the opening 12 of the camera 10. Therefore, according to the optical system 15, it is possible to obtain the dark pupil image. In the dark pupil image, the pupil P appears dark. Further, when the eye is irradiated with light having a wavelength with high transmittance, reflection of the light on the retina is increased. Therefore, the pupil P appears bright. On the other hand, when the eye is irradiated with light having a wavelength with low transmittance, the reflection of the light on the retina is decreased. Therefore, the pupil P appears dark. In the light source 13 of the line-of-sight detection device 1, the light emitting element 13a emits light having a wavelength with a high transmittance (a center wavelength is 850 nm). The light emitting element 13a is provided at a position adjacent to the opening 12. In addition, the light emitting element 13b emits light having a wavelength with a low transmittance of the eye (a center wavelength is 940 nm). The light emitting element 13b is provided at a position away from the opening 12.

When the bright pupil image is obtained, the lighting control unit 21 and the image input unit 22 light the light emitting element 13a according to the odd field of the camera 10. When the dark pupil image is obtained, the lighting control unit 21 and the image input unit 22 light the light emitting element 13b according to the even field of the camera 10. Further, the image input unit 22 slightly shifts the operation timing of the camera $10_L$ with respect to the operation timing of the camera $10_R$. An exposure time of the camera 10 is set to be equal to or shorter than a shift time. During the exposure time of the camera 10, the lighting control unit 21 causes the corresponding light emitting element 13a and light emitting element 13b to emit light alternately. According to this control, it is possible to suppress an influence of the light from the light source 13 of one camera 10 on the image of the other camera 10. In other words, according to this control, occurrence of crosstalk can be suppressed.

The image input unit 22 receives the bright pupil image and the dark pupil image obtained through the series of these controls from the camera 10. The input image has valid pixels only in the odd field or the even field. Therefore, the image input unit 22 embeds a luminance average of the pixel lines of the adjacent valid pixels into a pixel value between the lines. As a result, the image input unit 22 obtains the bright pupil image or the dark pupil image. The image input unit 22 outputs the bright pupil image and the dark pupil image obtained by the camera 10 to the calculation unit 23.

[Acquisition of Corneal Reflection Position $G_S$]

The preprocessing unit 26 obtains corneal reflection G from each of the bright pupil image and the dark pupil image input from the image input unit 22. Specifically, the preprocessing unit 26 binarizes and labels one image using a P tiling method. The preprocessing unit 26 obtains a plurality of corneal reflections G from the image using information on the shape, and luminance average, or the like. Through such a process, the preprocessing unit 26 obtains the corneal reflection G from each of the bright pupil image and the dark pupil image. Subsequently, the preprocessing unit 26 obtains a position $G_S$ of the corneal reflection in the bright pupil image and the dark pupil image using the corneal reflection G obtained from the bright pupil image and the dark pupil image.

The preprocessing unit 26 obtains the amount of position calibration. The amount of position calibration is the amount of movement of the corneal reflection between the bright pupil image and the dark pupil image. The amount of position calibration is based on an estimated or calculated position $G_S$ of the corneal reflection. Subsequently, the preprocessing unit 26 obtains a difference image. Specifically, the preprocessing unit 26 shifts an image of a previous field (an i-th field) to an image of a next field (a (i+1)-th field) by the amount of position calibration so that the positions $G_S$ of the two corneal reflections match each other. Then, the preprocessing unit 26 obtains a difference image from the two images. The preprocessing unit 26 obtains coordinates indicating the matched position $G_S$ of the corneal reflection, that is, the position $G_S$ of the cornea reflection based on the image coordinates.

[Acquisition of Position $P_S$ of Pupil Center]

The preprocessing unit 26 obtains the difference image using the bright pupil image and the dark pupil image. When the difference image is obtained, alignment between the bright pupil image and the dark pupil image may be performed using the amount of position calibration described above. Since this differential image includes an emphasized pupil P, the differential image is also called a pupil image. Subsequently, the preprocessing unit 26 specifies the position $P_S$ of the pupil center from the difference image. The difference image does not change greatly in luminance from the previous frame. Therefore, the preprocessing unit 26 binarizes the difference image with a value of half of the average luminance as a threshold value, using the luminance average of the pupil P detected in the previous frame. The preprocessing unit 26 performs labeling on the binarized difference image. Subsequently, the preprocessing unit 26 obtains the pupil P from the connected components of the labeled pixels using shape parameters such as the area, size, area ratio, degree of square, and pupil feature quantity of the pupil P. The preprocessing unit 26 obtains the position (coordinates) of the pupil center in the difference image.

Subsequently, the preprocessing unit 26 obtains three-dimensional coordinates of the pupil center. Specifically, the preprocessing unit 26 prepares two pupil images respectively obtained by the two cameras 10. Subsequently, the preprocessing unit 26 obtains the coordinates of the position $P_S$ of the pupil center in each of the two pupil images. Subsequently, the preprocessing unit 26 obtains three-dimensional coordinates of the position $P_S$ of the pupil center using a stereo method, by using the position $P_S$ of the pupil center.

In the stereo method, a position of a point in a space is determined for the coordinates of the point in the image. First, an object is imaged by using a plurality of cameras disposed at different positions. Then, the position in the space is determined by using internal parameters and external parameters of the camera. The internal parameters include a focal length of a lens of the camera, an image center, a pixel size, and the like. The external parameters include a position or attitude of the camera. Specifically, the preprocessing unit 26 obtains a relational equation between the coordinates of the position $P_S$ of the pupil center in the image coordinate system and the coordinates of the position $P_S$ of the pupil center in the world coordinate system in the three-dimensional space while referring to calibration data. Subsequently, the preprocessing unit 26 obtains three-dimensional coordinates of the position $P_S$ of the pupil center in the world coordinate system using a relational equation.

The preprocessing unit 26 extracts an outer edge portion of a region indicating the pupil P in the difference image. A process of extracting the outer edge portion is not particularly limited. The preprocessing unit 26 obtains an approximate equation for approximating the extracted shape as an ellipse. The preprocessing unit 26 obtains information on the major diameter $L_A$ and the minor diameter $L_B$ when the pupil P is regarded as an ellipse using the approximate equation.

Through the above process, information on the position $G_S$ of the corneal reflection and the position $P_S$ of the pupil center can be obtained. Using this information and the information recorded in the recording unit 24, the computation unit 27 obtains information that is used for a first line-of-sight detection process, a second line-of-sight detection process, and the visual axis calculation process.

As illustrated in FIG. 2, the second computation unit 27b sets a virtual viewpoint plane VS'-Y' using the three-dimensional position of the position $P_S$ of the pupil center. The virtual viewpoint plane VS'-Y' is a plane having the camera-pupil center vector OP as a normal. The camera-pupil center vector OP is a vector connecting an origin O to the position $P_S$ of the pupil center, with a center of the opening 12 of the camera 10 as the origin O. The virtual viewpoint plane VS'-Y' corresponds to the projection plane (an image plane) of the image captured by the camera 10. Here, an X' axis corresponds to an intersection line between an XW-ZW plane of a world coordinate system and the virtual viewpoint plane VS'-Y'.

The second computation unit 27b obtains a vector $r_G$ from the corneal reflection G on the image surface $S_G$ to the position $P_S$ of the pupil center. The second computation unit 27b converts the vector $r_G$ into the corneal reflection-pupil center vector r. The corneal reflection-pupil center vector r is a vector obtained by converting the vector $r_G$ to an actual magnitude using a magnification factor of the camera. The magnification factor of the camera is obtained from a distance of the camera-pupil center vector OP. In this case, it is assumed that each camera 10 is considered to be a pinhole model, and the position $G_S$ of the corneal reflection and the position $P_S$ of the pupil center are assumed to be on a plane parallel to the virtual viewpoint plane VS'-Y'. That is, the second computation unit 27b obtains the corneal reflection-pupil center vector r. The corneal reflection-pupil center vector r indicates relative coordinates of the position $P_S$ of the pupil center and the position $G_S$ of the corneal reflection. The relative coordinates are the coordinates on the plane parallel to the virtual viewpoint plane VS'-Y' and including the three-dimensional coordinates of the position $P_S$ of the pupil center. Further, the corneal reflection-pupil center vector r indicates an actual distance from the position $G_S$ of the corneal reflection to the position $P_S$ of the pupil center.

[First Line-of-Sight Detection Process]

The first line-of-sight detection process is executed in the first optical axis acquisition unit 28. The first optical axis acquisition unit 28 obtains the first optical axis candidate using the cornea reflection-pupil center method. In the first line-of-sight detection process, the first optical axis acquisition unit 28 obtains an angle θ corresponding to the optical axis AL shown in Equation (12).

[Math. 12]

$$\theta = kr \quad (12)$$

In Equation (12), the corneal reflection-pupil center vector r is known since the corneal reflection-pupil center vector r is obtained by the second computation unit 27b. A slope φ which is a component of the angle θ is an angle formed by the corneal reflection-pupil center vector r and the horizontal axis X'. Therefore, the slope φ is known. Then, the angle θ is obtained by obtaining the magnitude |θ| of the angle θ. The magnitude |θ| of the angle θ is obtained using Equation (13).

[Math. 13]

$$\theta = k|r| \quad (13)$$

That is, the magnitude |θ| of the angle θ is obtained by calculating an absolute value of the corneal reflection-pupil center vector r and multiplying the absolute value by a first coefficient k. Through the above process, the magnitude |θ| of the angle θ and the slope φ of the angle θ are obtained. As a result, the angle θ as the first optical axis candidate is obtained.

[Second Line-of-Sight Detection Process]

A second line-of-sight detection process is executed in the second optical axis acquisition unit 29. The second optical axis acquisition unit 29 obtains the second optical axis candidate by using the pupil shape method. In the pupil shape method, an angle θ corresponding to the optical axis AL is obtained. In the pupil shape method, it is assumed that the magnitude |θ| which is a component of the angle θ corresponds to a slope $\theta_S$ (see FIG. 3(b)). The slope $\theta_S$ is obtained by using Equation (14).

[Math. 14]

$$\theta_S = \cos^{-1}\left(\frac{\text{minor diameter}}{\text{major diameter}}\right) = \cos^{-1}\left(\frac{1}{\text{ellipticity}}\right) \quad (14)$$

In the pupil shape method, it is assumed that the slope φ which is a component of the angle θ corresponds to the slope γ' (see FIG. 4). The second optical axis acquisition unit 29 obtains a slope γ' using a direction of the minor axis. Through the above-described process, the slope $\theta_S$ corresponding to the magnitude |θ| of the angle θ and the slope γ' corresponding to the slope φ of the angle θ are obtained. As a result, the angle θ as the second optical axis candidate is obtained.

[Selection of Line-of-Sight Detection Process]

The optical axis information acquisition unit 31 selects any one of a process based on the corneal reflection-pupil center method and a process based on the pupil shape method as the line-of-sight detection process. This selection is based on the magnitude |θ| of the angle θ formed by the camera-pupil center vector OP and the optical axis AL (the line-of-sight vector PT). Specifically, when the magnitude |θ| of the angle θ is small, the optical axis information acquisition unit 31 selects the corneal reflection-pupil center method. This is because when the magnitude |θ| of the angle θ is small (θ≈0), a shape of an outer peripheral edge of the pupil P in the difference image approximates to a circular shape. That is, the difference between the major diameter and the minor diameter decreases. Therefore, a variation in the slope $\theta_S$ obtained from the ellipticity R tends to increases. This is because the slope $\theta_S$ is an inverse cosine component of the reciprocal of the ellipticity R. Therefore, when the magnitude |θ| of the angle θ is small (θ≈0), the corneal reflection-pupil center method can obtain a better result than the pupil shape method. On the other hand, the optical axis information acquisition unit 31 selects the pupil shape method when the magnitude $|\theta|$ of the angle $\theta$ is great. This is because, when the magnitude $|\theta|$ of the angle $\theta$ increases, a variation in the slope $\theta_S$ obtained from the ellipticity R tends to be small. Therefore, when the magnitude $|\theta|$ of the angle $\theta$ is great, the pupil shape method can obtain a better result than the corneal reflection-pupil center method.

Further, in the corneal reflection-pupil center method, when the magnitude $|\theta|$ of the angle $\theta$ is small, linearity (see Equation (1)) between the angle $\theta$ and the corneal reflection-pupil center vector r is high. Therefore, it is easy for detection accuracy of the line of sight to be made high. On the other hand, when the magnitude $|\theta|$ of the angle $\theta$ is great, it may be difficult to detect the corneal reflection G. Further, even when the corneal reflection G appears, non-linearity appears and it is easy for white eye reflection to be erroneously detected due to image processing in a case in which the corneal reflection G is formed on the peripheral portion of the cornea.

Therefore, the image processing device 20 sets a threshold value. This threshold value is used to distinguish between a range in which linearity is dominant in the relationship between the corneal reflection-pupil center vector r and the angle $\theta$ (a range in which the corneal reflection G appears in most of the subjects M) and a range in which non-linearity is dominant in the relationship between the corneal reflection-pupil center vector r and the angle $\theta$. The magnitude $|\theta|$ of the angle $\theta$=about 30 degrees is exemplified as the threshold value. The threshold value is not limited to 30 degrees, and a desired value may be used. The image processing device 20 obtains the magnitude $|\theta|$ of the angle $\theta$ for selecting the line-of-sight detection process by using the ellipticity R of the pupil P. Specifically, the image processing device 20 obtains a slope $\theta_S$ corresponding to the magnitude $|\theta|$ of the angle $\theta$. When the slope $\theta_S$ obtained from the ellipticity R is smaller than the threshold value, the optical axis information acquisition unit 31 selects a result of the corneal reflection-pupil center method and outputs the first optical axis candidate to the visual axis acquisition unit 32. On the other hand, when the slope $\theta_S$ obtained from the ellipticity R is greater than the threshold value, the optical axis information acquisition unit 31 selects a result of the pupil shape method and outputs the second optical axis candidate to the visual axis acquisition unit 32.

[Process of Acquiring Visual Axis]

A process of acquiring the visual axis is executed in the visual axis acquisition unit 32. The process of acquiring the visual axis is a process of calibrating a deviation of the optical axis AL from the visual axis AS. For example, when the first optical axis candidate is output to the visual axis acquisition unit 32 as the optical axis AL1, the visual axis acquisition unit 32 performs a process shown in Equation (15). That is, the visual axis acquisition unit 32 executes a vector calculation for subtracting the deviation angle $\theta_0$ from the angle $\theta_{AL1}$ as the optical axis AL. In Equation (15), the slope $\theta_S$ is the visual axis AS. The angle $\theta_{AL1}$ is the first optical axis candidate.

[Math. 15]

$$\theta_S = \theta_{AL} - \theta_0 \qquad (15)$$

When the second optical axis candidate is output as the optical axis AL to the visual axis acquisition unit 32, the visual axis acquisition unit 32 performs the process shown in Equation (16). That is, the visual axis acquisition unit 32 executes a vector calculation for subtracting the deviation angle $\theta_0$ from the angle $\theta_{AL2}$ as the optical axis AL. In Equation (16), the slope $\theta_S$ is the visual axis AS. The angle $\theta_{AL2}$ is the second optical axis candidate.

[Math. 16]

$$\theta_S = \theta_{AL2} - \theta_0 \qquad (16)$$

The line-of-sight detection device 1 includes a first optical axis acquisition unit 28 and a second optical axis acquisition unit 29. The first optical axis acquisition unit 28 obtains the optical axis AL using the position $P_S$ of the pupil center and the position $G_S$ of the corneal reflection. Therefore, the line-of-sight detection device 1 can perform line-of-sight detection in a range of the line of sight in which the corneal reflection G is obtained. The second optical axis acquisition unit 29 obtains the optical axis AL using the shape of the pupil P. Therefore, the line-of-sight detection device 1 can perform line-of-sight detection even in a range of the line of sight in which the corneal reflection G cannot be obtained. The optical axis information acquisition unit 31 obtains information for selecting any one of the first optical axis acquisition unit 28 and the second optical axis acquisition unit 29 using the shape of the pupil P. In the visual axis acquisition unit 32, a deviation between the optical axis AL and the visual axis AS of the selected optical axis candidate is calibrated, and the visual axis AS as a line of sight is obtained. Therefore, the line-of-sight detection device 1 can extend the range in which the line of sight can be satisfactorily detected, from a narrow line-of-sight range in which the corneal reflection G can be obtained to a wide line-of-sight range in which the corneal reflection G cannot be obtained.

That is, according to the line-of-sight detection device 1, it is possible to execute the corneal reflection-pupil center method and the pupil shape method on the same platform (a foundation or a basic theory).

In the corneal reflection-pupil center method, the line of sight (or a gazing point) is detected by using the relative position between the position $G_S$ of the corneal reflection and the position $P_S$ of the pupil center obtained from the image. In the pupil shape method, the line of sight (or the gazing point) is detected by using the shape of the pupil P defined by the ellipticity R and the direction of the minor axis.

Specifically, in the corneal reflection-pupil center method, three-dimensional coordinates of the pupil P is obtained using the optical system 15 in which the camera 10 is calibrated. Next, the corneal reflection-pupil center method obtains the angle $\theta$ between the camera-pupil center vector OP and the optical axis AL of the eyeball 50. These are obtained using the corneal reflection-pupil center vector OP and the corneal reflection-pupil center vector r obtained from the image. On the other hand, in the pupil shape method, first, three-dimensional coordinates of the pupil P are obtained. Then, in the pupil shape method, the camera-pupil center vector OP is obtained. Then, the angle $\theta$ is obtained. The angle $\theta$ is obtained using the ellipticity R of the ellipse indicating the outer shape of the pupil P and the direction of the minor axis. Therefore, according to the line-of-sight detection device 1, the corneal reflection-pupil center method and the pupil shape method can be executed on the same platform.

Further, the line-of-sight detection device 1 causes the subject M to gaze at a visual target for calibration of which coordinates are known in the cornea reflection-pupil center method. As a result, the line-of-sight detection device 1 obtains the deviation between the visual axis AS (the direction vector of the visual axis AS) and the optical axis AL (the direction vector of the optical axis) as the deviation angle $\theta_0$. A process of obtaining this deviation is called user calibration or gazing point calibration. When the line-of-sight detection process (or the gazing point detection process) is performed, an output result acquired as the optical axis AL is calibrated using the deviation angle $\theta_0$. As a result, it is possible to obtain the visual axis AS. Similarly, in the pupil shape method, it is possible to use the deviation angle $\theta_0$ clarified by user calibration for calibration of the output result acquired as the optical axis AL.

More specifically, the line-of-sight detection device 1 performs calibration of the deviation between the visual axis AS and the optical axis AL at a rear stage in the process of obtaining the line of sight. In other words, the line-of-sight detection device 1 performs a calibration process after the process of obtaining the optical axis AL. According to this configuration, even when processes of obtaining the optical axis AL are different processes, a result obtained from these processes is the optical axis AL. Therefore, it is possible to easily execute the calibration process.

It should be noted that the calibration process may be a process of calibrating by viewing one point (a one-point calibration method) or may be another process. Then, for example, when the visual target presented at the center of the screen is viewed for a moment, the corneal reflection-pupil center method is executed. As a result, calibration information (deviation angle $\theta_0$) is obtained. In a case in which the subject M views a position greatly far away from the optical system 15, the calibration information (the deviation angle $\theta_0$) can also be used even when the pupil shape method is applied. Therefore, a burden on the subject M with respect to the calibration can be reduced. Further, the line-of-sight detection in a wide angle range becomes possible as compared with a case in which only the corneal reflection-pupil center method is used.

According to an experiment of the inventors, a range in which predetermined line-of-sight detection accuracy in the line-of-sight detection device 1 can be obtained is +45 degrees in the horizontal direction with reference to the corneal reflection-pupil center vector OP. This range was confirmed by actually performing experiments. Further, it is assumed that the size $|\theta|$ of the angle $\theta=60$ degrees as a detection range. In this case, the ellipticity R (the ratio of the minor diameter to the major diameter) is 0.5. Therefore, by improving the image processing and controlling the light source, at least about $|\theta|=60$ degrees can be measured. It should be noted that examples of a remote line-of-sight detection device or gazing point detection device of which the detection range is 45 degrees or more have not been reported.

[Acquisition of First Coefficient k]

In the above description, the first coefficient k is included in Equation (17) of the corneal reflection-pupil center method.

[Math. 17]

$$\theta = k|r| \quad (17)$$

The first coefficient k may be treated as a constant value. Further, the first coefficient k may be treated as a changing value. For example, when the angle $\theta$ is small, a relationship between the angle $\theta$ and the corneal reflection-pupil center vector r has a high linearity in Equation (17). Therefore, the first coefficient k is treated as a constant value. On the other hand, when the angle $\theta$ is large, the relationship between the angle $\theta$ and the corneal reflection-pupil center vector r is has storing nonlinearity in Equation (17). Therefore, the first coefficient k is treated as a value that changes according to the corneal reflection-pupil center vector r. Further, the first coefficient k changes according to personality of the eyeball 50 of the subject M.

[Acquisition of First Coefficient k as Constant Value]

Now, when the subject M views any point on the display device 30, Equation (18) is obtained for each of the cameras 10. Here, the camera $10_L$ is disposed at a position ($O_{S1}$), and the camera $10_R$ is disposed at a position ($O_{S2}$). The corneal reflection G occurring in the left eye (first eye) is a position ($G_{S1}$) and the corneal reflection G occurring in the right eye (second eye) is a position ($G_{S2}$). Further, a pupil center position of the left eye is a position ($P_{S1}$). A pupil center position of the right eye is a position ($P_{S2}$). An angle $\theta_1$ indicates the visual axis AS obtained from the camera $10_L$. An angle $\theta_1'$ indicates the optical axis AL obtained from the camera $10_L$. The angle $\theta_0$ indicates the deviation angle. A corneal reflection-pupil center vector $r_1$ (a third vector) indicates a vector obtained from the camera $10_L$. An angle $\theta_2$ indicates the visual axis AS obtained from the camera $10_R$. The angle $\theta_2'$ indicates the optical axis AL obtained from the camera $10_R$. A corneal reflection-pupil center vector $r_2$ (a fifth vector) indicates a vector that is obtained from the camera $10_R$. Here, in Equation (18), since the first coefficient k and the deviation angle $\theta_0$ are unique to the eyeball, the first coefficient k and the deviation angle $\theta_0$ are common.

[Math. 18]

$$\theta_1 = \theta_1' - \theta_0 = kr_1 - \theta_0$$

$$\theta_2 = \theta_2' - \theta_0 = kr_2 - \theta_0 \quad (18)$$

Equation (19) is obtained from Equation (18).

[Math. 19]

$$\theta_2 - \theta_1 = \theta_2' - \theta_1' = k(r_2 - r_1) \quad (19)$$

$$k = \frac{\theta_2' - \theta_1'}{r_2 - r_1}$$

In Equation (19), the first coefficient k is a positive real number. Therefore, Equation (19) is shown as Equation (20).

[Math. 20]

$$k = \left|\frac{\theta_2' - \theta_1'}{r_2 - r_1}\right| = \frac{|\theta_2 - \theta_1|}{|r_2 - r_1|} \quad (20)$$

In Equation (20), a numerator ($|\theta_2 - \theta_1|$) on the rightmost side is an angle between the two optical systems 15 as viewed from the pupil P. Therefore, it is possible to obtain the first coefficient k as a constant value by using Equation (20). It should be noted that according to Equation (20), even when the subject M views any visual target, the first coefficient k can be obtained for each frame.

[Acquisition of First Coefficient k as Variable Value]

When a relationship between the magnitude $|r|$ of the corneal reflection-pupil center vector r and the angle $\theta$ is nonlinear, Equation (17) is shown as Equation (21).

[Math. 21]

$$\theta = f(r) \quad (21)$$

Further, Equation (21) is shown as Equation (22). In Equation (22), a function f is a nonlinear function. Therefore, when the function f is known, the first coefficient k can be obtained. Next, a method for obtaining the function f will be described.

[Math. 22]

$$k = \frac{f(\theta_2) - f(\theta_1)}{r_2 - r_1} \quad (22)$$

First, the function f indicates $|\theta|$ which is the magnitude of the angle $\theta$ and the magnitude $|r|$ of the corneal reflection-pupil center vector r. In Equation (22), the slope $\phi'$ of the corneal reflection-pupil center vector r and the slope $\phi$ of the angle $\theta$ match each other. In other words, Equation (23) is obtained.

[Math. 23]

$$|\theta| = \theta = f(|r|) \quad (23)$$

Figure 11:
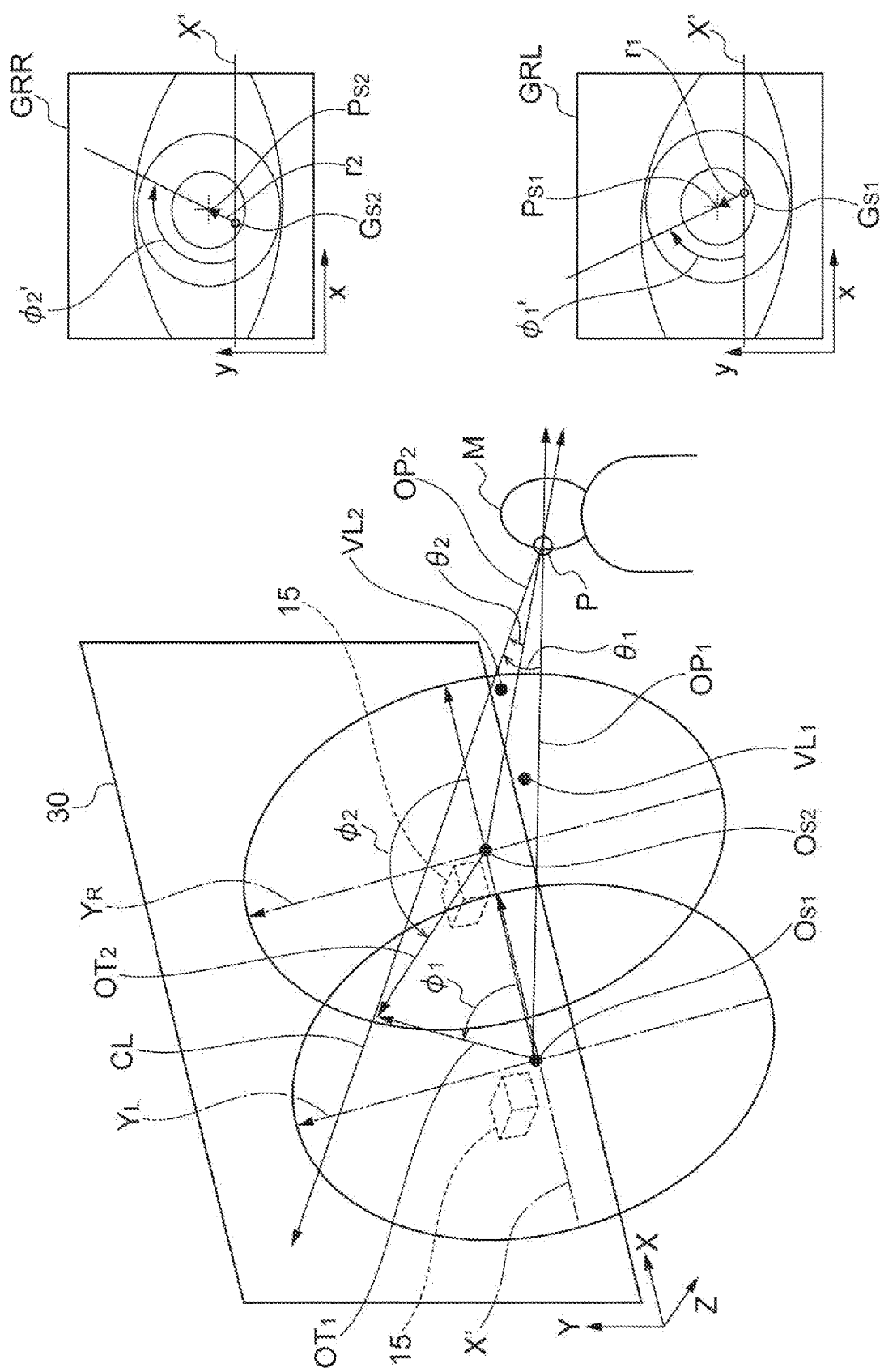
FIG. 11 is a diagram illustrating a method of obtaining a first coefficient.

According to Equation (23) above and the assumption, the slope $\phi'$ of the corneal reflection-pupil center vector r is obtained using the image obtained by the camera 10 and the internal parameters of the camera. In FIG. 11, two virtual optical axis planes $VL_1$ and $VL_2$ are shown for the two optical systems 15. The intersection line CL of the virtual optical axis planes $VL_1$ and $VL_2$ corresponds to the optical axis AL. The virtual optical axis plane $VL_1$ includes a position $(O_{S1})$ of the first camera, a position $(P_{S1})$ of the pupil center, and a position at which the first optical axis intersects the first virtual viewpoint plane. The first virtual viewpoint plane is a plane having a fourth vector directed from the first camera position $(O_{S1})$ to the position $(P_{S1})$ of the pupil center as a normal. The virtual optical axis plane $VL_2$ includes the position $(O_{S2})$ of the second camera, the position $(P_2)$ of the pupil center, and a position at which the second optical axis intersects the second virtual viewpoint plane. The second virtual viewpoint plane is a plane having a sixth vector directed from the second camera position $(O_{S2})$ to the position $(P_{S2})$ of the pupil center as a normal.

According to the method of obtaining the optical axis AL, the optical axis AL can be obtained irrespective of the magnitude $|r|$ of the corneal reflection-pupil center vector r and the magnitude $|\theta|$ of the angle $\theta$. Obtaining the optical axis AL corresponds to obtaining the angle $\theta$ with respect to the optical system 15. Therefore, a first coefficient $(k_1)$ corresponding to the left eye is obtained by using the fifth angle $(\theta_k)$ and the magnitude $(|r_1|)$ of the third vector $(r_1)$. The fifth angle $(\theta_k)$ is obtained from the intersection line at which the first virtual optical axis plane and the second virtual optical axis plane intersect each other and the fourth vector. Further, a first coefficient $(k_2)$ corresponding to the right eye is obtained using the fifth angle $(\theta_2)$ obtained from the intersection line and the sixth vector and the magnitude $(|r_2|)$ of the fifth vector $(r_2)$.

The corneal reflection-pupil center vectors $r_1$ and $r_2$ are also obtained from the respective optical systems 15. Therefore, it is possible to determine the nonlinear function f shown in Equation (23) by plotting a relationship between the magnitude $|r|$ of the corneal reflection-pupil center vector r and the magnitude $|\theta|$ of the angle $\theta$. It should be noted that the relationship between the magnitude $|r|$ of the corneal reflection-pupil center vector r and the magnitude $|\theta|$ can be determined regardless of which direction the subject M is viewing. Therefore, it is possible to accumulate data while the subject M is viewing various directions. It should be noted that in this case, it is assumed that the position $G_S$ of the corneal reflection and the position $P_S$ of the pupil center can both be detected.

After the function f is acquired, the angle $\theta$ is obtained from the image acquired by the camera 10 using the corneal reflection-pupil center vector r. Therefore, the optical axis AL of the eyeball 50 can be obtained for each camera 10. It should be noted that the function f acquired in advance may be repeatedly used. Further, the function f may be updated each time data is increased. When the subject M is caused to gaze at a visual target of which coordinates are known, the angle $\theta$ is obtained. At the same time, since the pupil P is obtained, it is possible to obtain the visual axis AS passing through the pupil P and the visual target position.

[Acquisition of Second Coefficient h]

In the above description, the pupil shape method does not include a coefficient corresponding to the first coefficient k in the corneal reflection-pupil center method. However, also in the pupil shape method, it is possible to include the second coefficient h corresponding to the first coefficient k as in Equation (24).

[Math. 24]

$$\theta = h\theta' - \theta_0 \quad (24)$$

The second coefficient h may be treated as a constant value, similar to the first coefficient k. Further, the second coefficient h may be treated as a changing value. The second coefficient h is obtained by the same method as the method for the first coefficient k.

The pupil P observes an object through the lens called the cornea. Therefore, as the angle of the line of sight with respect to the camera 10 increases, a relationship between the ellipticity R and the angle $\theta$ deviates due to refraction of light caused by the cornea. Therefore, nonlinear calibration is required in the relationship between the ellipticity R and the angle $\theta$. According to the process of acquiring the first coefficient k, the virtual optical axis planes $VL_1$ and $VL_2$ are obtained from information on only a minor-axis direction of the ellipse of the pupil P. Therefore, the process of acquiring the first coefficient k is not affected by the refraction. That is, it is not necessary to take refraction into consideration in the process of acquiring the first coefficient k.

[Acquisition of Calibration Information]

The line-of-sight detection process is executed by repeating steps S11 to S18 described above. In the above description, the calibration information indicating the deviation between the optical axis AL and the visual axis AS has been described as the deviation angle $\theta_0$. This deviation angle $\theta_0$ is acquired in the calibration step that is performed before a repetitive process including steps S11 to S18.

Figure 12:
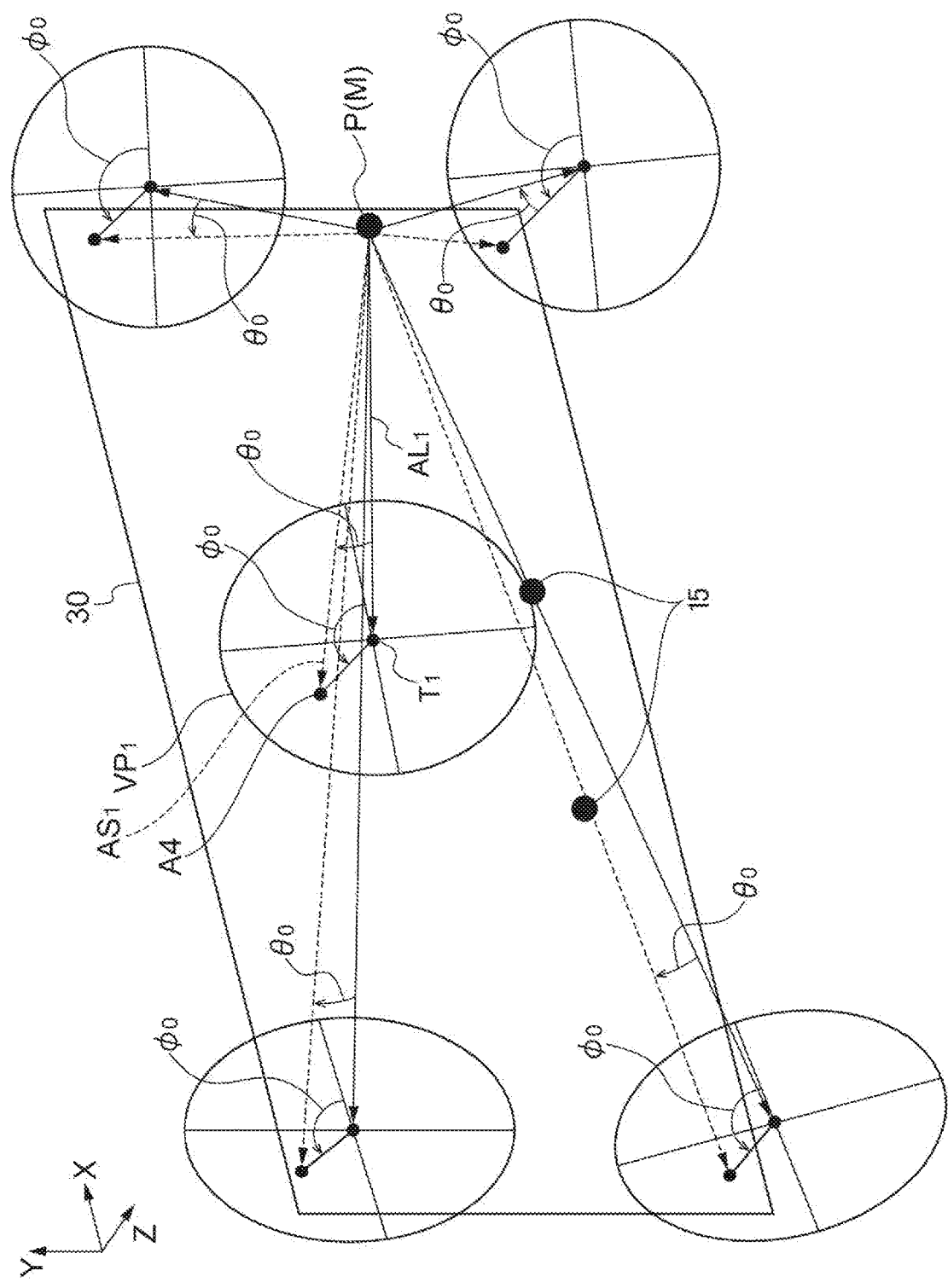
FIG. 12 is a diagram illustrating another method of obtaining an optical axis.

As illustrated in FIG. 12, when the subject M views a visual target A4 at a center, a visual axis $AS_1$ directed from the pupil P of the subject M to the visual target A4 is formed. On the other hand, the optical axis AL1 is obtained by executing another process. An intersection $T_1$ between the optical axis AL1 and the display device 30 is obtained. FIG. 12 illustrates a virtual plane with the intersection $T_1$ as an origin. This virtual plane is obtained by replacing the position of the camera of the virtual viewpoint plane in FIG. 12 with an intersection between the optical axis AL of the eyeball and the display. In this case, an intersection line between the virtual plane $VP_1$ and an XZ plane (a horizontal plane) of the world coordinate system is defined as a horizontal axis of the virtual plane $VP_1$. An intersection of the virtual plane $VP_1$ and the visual axis AS is obtained.

Conversion into a vector in a coordinate system of the virtual viewpoint plane is performed. As a result, calibration information (deviation angle $\theta_0$) indicating the deviation between the visual axis AS and the optical axis AL is obtained.

The present invention has been described in detail based on the embodiment thereof. However, the present invention is not limited to the above embodiment. The present invention can be variously modified without departing from the gist thereof.

Modification Example 1

Figure 13:
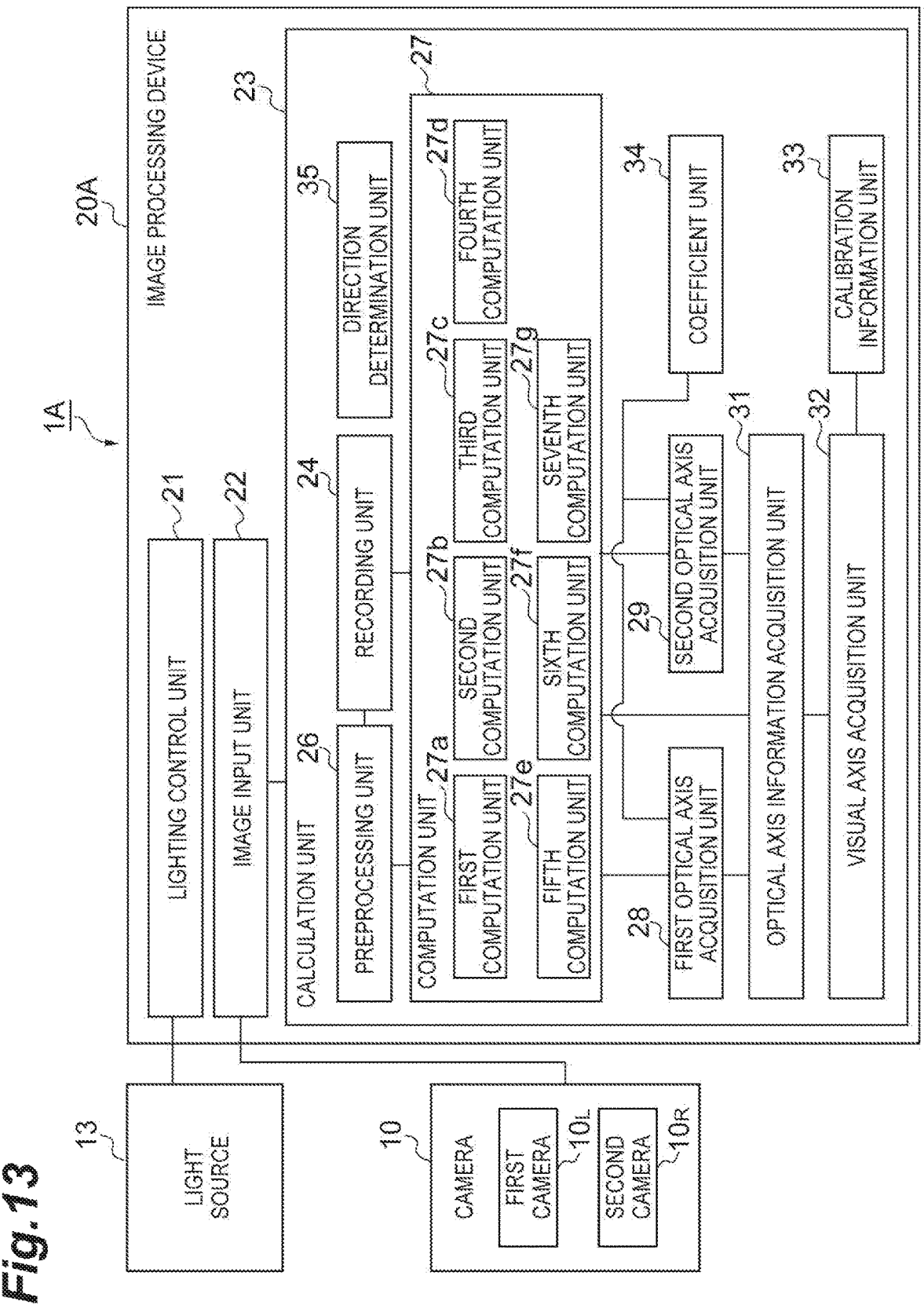
FIG. 13 is a functional block diagram illustrating a line-of-sight detection device according to a modification example.

As illustrated in FIG. 13, the image processing device 20A of the line-of-sight detection device 1 may include a direction determination unit 35. The direction determination unit 35 determines the direction of the visual axis AS with respect to the camera-pupil center vector OP.

Figure 14:
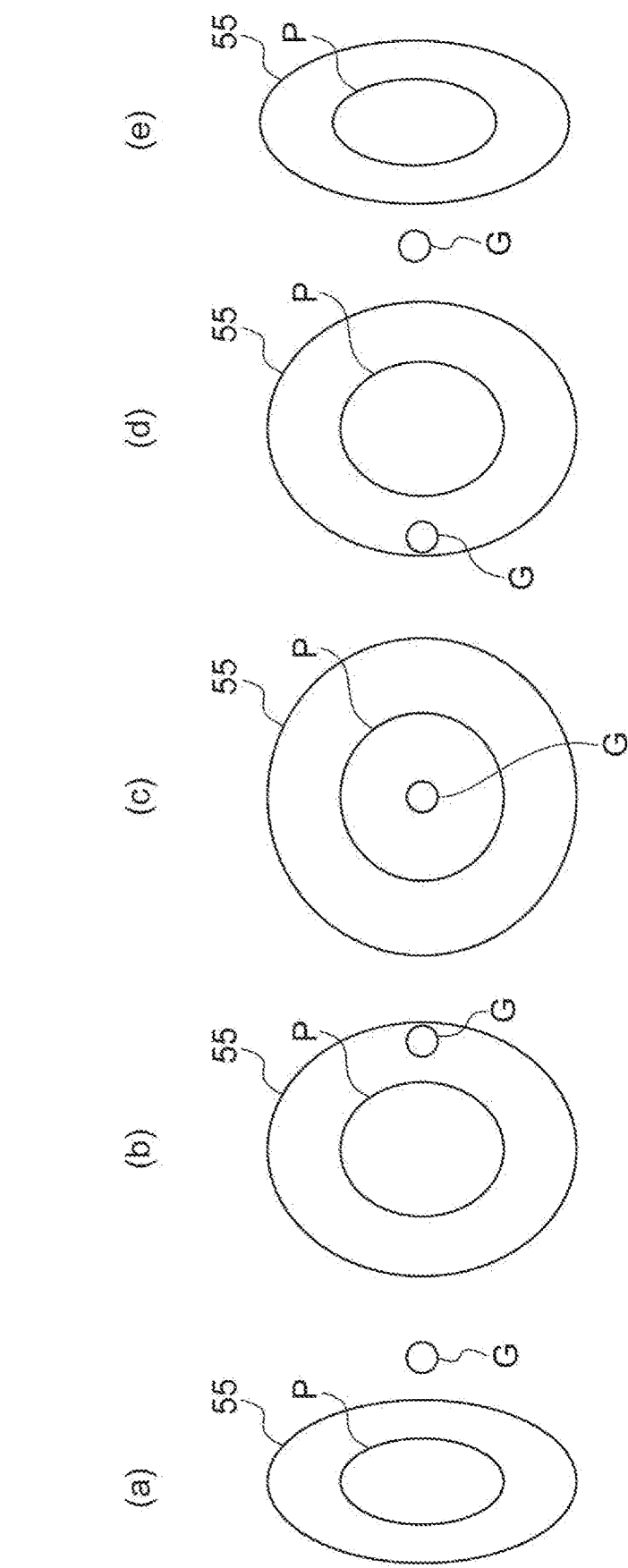
FIG. 14 is a diagram illustrating a principle of detecting the line-of-sight direction.

FIG. 14(a), (b), (c), and (d) illustrate a positional relationship between the pupil P of the subject M, a glow 55, and the corneal reflection G. FIG. 14(a) illustrates a positional relationship among the pupil P, the glow 55, and the corneal reflection G when the subject M views the visual target on the right side of the camera 10. FIG. 14(b) illustrates a positional relationship among the pupil P, the glow 55, and the corneal reflection G when the subject M is viewing the visual target at a position on the right side of the camera 10 and closer to the camera 10 relative to the visual target in FIG. 14(a). FIG. 14(c) illustrates a positional relationship among the pupil P, the glow 55, and the corneal reflection G when the subject M views the camera 10 or the light source 13. FIG. 14(d) illustrates a positional relationship among the pupil P, the glow 55, and the corneal reflection G when the subject M views the visual target on the left side of the camera 10. FIG. 14(e) illustrates a positional relationship among the pupil P, the glow 55, and the corneal reflection G when the subject M is viewing the visual target at a position on the left side of the camera 10 and farther from the camera 10 relative to the visual target in FIG. 14(d).

As illustrated in FIGS. 14(a) and 14(e), the reflection image (the corneal reflection G) of the light emitted from the light source 13 is generated outside the cornea. That is, the reflected image of the light emitted from the light source 13 is generated in a white eye region. As illustrated in FIGS. 14(b) and 14(d), a reflection image of the light emitted from the light source 13 is generated at a position away from the pupil P on the cornea. As illustrated in FIG. 14(c), a reflection image of the light emitted from the light source 13 is generated at a position close to the pupil P on the cornea.

As illustrated in FIGS. 14(a) and 14(d), the reflection image generated in the white eye region is not stabilized due to nonuniformity of the shape of the white eye or the like. Therefore, the reflection image generated in the white eye region is not suitable for use in high-precision eye-line-of-sight detection. For example, a method of determining whether the subject views the right or views the left according to whether the reflection image generated in the white eye region exists on the left or right side of the pupil P is known. However, in an eyeglass reflection image of the light source generated when the subject wears eyeglasses, the characteristics of the image greatly changes according to the eyeglasses, the subject M, and an angle of the head of the subject M. In addition, the white eye reflection also changes. Therefore, it may be difficult to distinguish between the subject viewing the right and subject viewing the left using characteristics of the image. Further, white eye reflection may not appear according to the line-of-sight direction. Therefore, according to a determination of the line-of-sight direction using the reflected image, it may be difficult to determine the line-of-sight direction.

When FIG. 14(a) is compared with FIG. 14(e), the shape of the pupil P in the image is the same either when the subject views a left index or when the subject views a right index. Specifically, the ellipticity R indicating the shape of the pupil P is the same either when the subject views a left index or when the subject views a right index as long as the angle of the visual axis AS with respect to the camera-pupil center vector OP is the same. That is, in the method of using the ellipticity R of the pupil P, when the subject views indices at point-symmetric positions with the optical system 15 interposed therebetween (for example, upper right and lower left), both cases cannot be distinguished since the cases indicate the same value of the ellipticity R.

Figure 15:
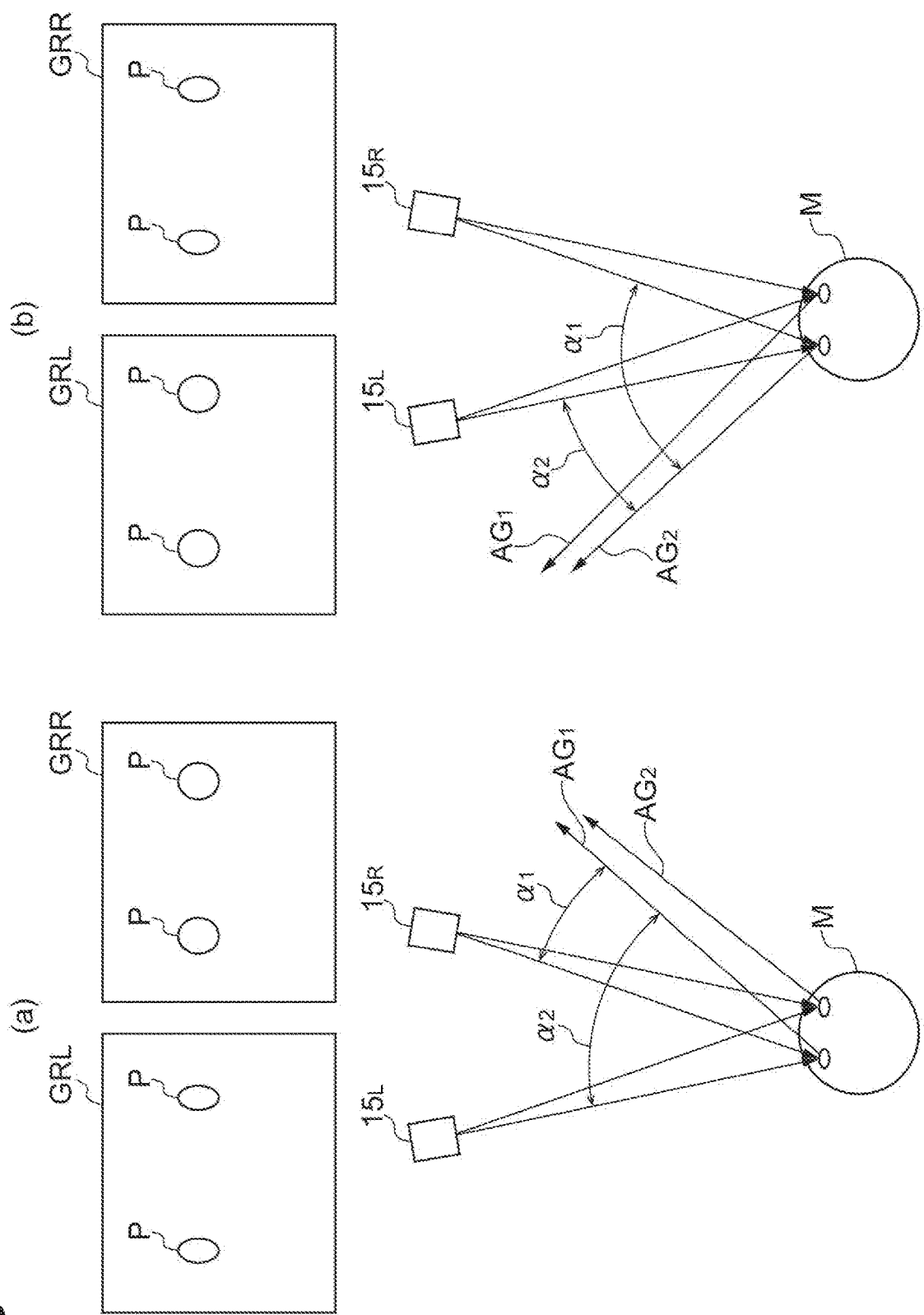
FIG. 15 is a diagram illustrating a principle of detecting a line-of-sight direction.

Therefore, the image processing device 20A may include the direction determination unit 35. The direction determination unit 35 discriminates the line-of-sight direction with respect to the camera-pupil center vector OP. FIG. 15(a) illustrates a case in which the subject M views the right side of the two optical systems $15_L$ and $15_R$ that are horizontally disposed. In this case, a slope $\alpha_1$ is greater than a slope $\alpha_2$. The slope $\alpha_1$ is a slope between the left optical system $15_L$ of the subject M and a line of sight $AG_1$ of the left eye. The slope $\alpha_2$ is a slope between the right optical system $15_R$ and the line of sight $AG_2$ of the left eye. As a result, the ellipticity $R_2$ obtained from the image GRR of the right optical system $15_R$ is greater than the ellipticity $R_1$ obtained from the image GRL of the left optical system $15_L$. The same may apply to the right eye. Conversely, as illustrated in FIG. 15(b), when the subject M greatly views the left side, the ellipticity $R_2$ obtained from the image GRR of the right optical system $15_R$ is greater than the ellipticity $R_1$ obtained from the image GRL of the left optical system $15_L$. According to this method, rough distinguishment between the subject M viewing the right or viewing the left can be performed by comparing the ellipticity $R_1$ and $R_2$ of the pupil P included in the images GRL and GRR respectively acquired by the left and right optical systems $15_L$ and $15_R$ with each other.

Modification Example 2

The line-of-sight detection device 1 is not limited to the configuration of the functional block diagram illustrated in FIG. 9. The line-of-sight detection device 1 may appropriately change a relationship between the respective functional blocks for efficiency of the process and the like. For example, in the line-of-sight detection device 1, the first optical axis acquisition unit 28 and the second optical axis acquisition unit 29 may include a first computation unit 27a, a second computation unit 27b, a third computation unit 27c, a fourth computation unit 27d, a fifth computation unit 27e, a sixth computation unit 27f, and a seventh computation unit 27g constituting the computation unit 27. Further, the line-of-sight detection method is not limited to an order shown in the flowchart of FIG. 10, and the order of each step may be changed. For example, in the line of sight detection method, before the optical axis candidates are obtained in the first optical axis acquisition unit 28 and the second optical axis acquisition unit 29, the optical axis acquisition unit may be selected and the optical axis AL may be obtained only in the selected optical axis acquisition unit. Further, in the line of sight detection method, the process of calibrating the optical axis may be executed immediately after the first optical axis candidate is obtained, and the process of calibrating the optical axis may be executed immediately after the second optical axis candidate is obtained. In this case, in the line-of-sight detection method, the calibration process is executed twice in the process of obtaining one visual axis AS.

Modification Example 3

Meanwhile, the second optical axis acquisition unit 29 of the line-of-sight detection device 1 according to the embodiment obtains the optical axis using the pupil shape. The pupil P is covered by the cornea 52 (see FIG. 5). As a result, the camera 10 outputs an image of the pupil P via the cornea 52. Then, refraction is likely to occur when the light passes through the cornea 52. Therefore, the position of the corneal contour on the image is likely to be deviated with respect to the position of the actual pupil contour. Therefore, the line-of-sight detection device 1 corrects the ellipticity R. As a result, a deviation of the position of the pupil contour on the image with respect to a position of the actual pupil contour is corrected. Specifically, the line-of-sight detection device 1 obtains the corrected ellipticity R' obtaining by correcting the ellipticity R. The line-of-sight detection device 1 performs the line-of-sight detection process using the corrected ellipticity R'. The correction of the ellipticity R may be executed by the second optical axis acquisition unit 29. In addition, the correction of the ellipticity R may be executed by the fourth computation unit 27*d* that obtains the ellipticity R. For example, Equation (25) is used for correction of the ellipticity R.

[Math. 25]

$$R' = a \times R^2 + b \times R \quad (25)$$

In Equation (25), R' is a corrected ellipticity. R is an ellipticity. a and b are coefficients. These coefficients a and b may be experimentally obtained. As an example, a=0.3 and b=0.7 may be used. Further, a construction of a mathematical equation is not limited to Equation (25) as long as an influence of refraction at the cornea 52 can be corrected.

The second optical axis acquisition unit 29 may obtain the slope $\theta_S$ by directly using the inverse cosine component of the reciprocal of the ellipticity R (see Equation (7)).

The second optical axis acquisition unit 29 may obtain the slope $O_S$ by directly using the inverse cosine component of the reciprocal of the corrected ellipticity R' (see Equation (26)).

[Math. 26]

$$\theta_S = \cos^{-1}\left(\frac{1}{R'}\right) \quad (26)$$

As shown in Equation (27), the second optical axis acquisition unit 29 may multiply the inverse cosine component of the reciprocal of the corrected ellipticity R' by the second coefficient (h). As a result, a slope $\theta_S$ is also obtained as a corrected value.

[Math. 27]

$$\theta_S = h \times \cos^{-1}\left(\frac{1}{R'}\right) \quad (27)$$

According to such a line-of-sight detection device 1, it is possible to further improve the accuracy of the line-of-sight detection based on the pupil shape method.

Modification Example 4

The line-of-sight detection device 1 according to the present embodiment also executes a process based on the pupil shape method on a platform that performs a process based on the cornea reflection-pupil center method. That is, the line-of-sight detection device 1 according to the present embodiment executes a process based on the cornea reflection-pupil center method and a process based on the pupil shape method on one platform. However, the present invention is not limited to such a platform, and the process based on the corneal reflection-pupil center method and the process based on the pupil shape method may be executed on a platform that executes another process.

For example, the process based on the corneal reflection-pupil center method and the process based on the pupil shape method may be executed on a platform that obtains a face posture of the subject M. The "face posture" referred to herein means a position and a direction of a skull of the subject M. The face posture is not related to a direction (for example, line of sight) of the eyeball of the subject M. For example, there is a Patent Literature (Japanese Unexamined Patent Publication No. 2007-26073) of the inventors as a technology for detecting a face posture.

Figure 16:
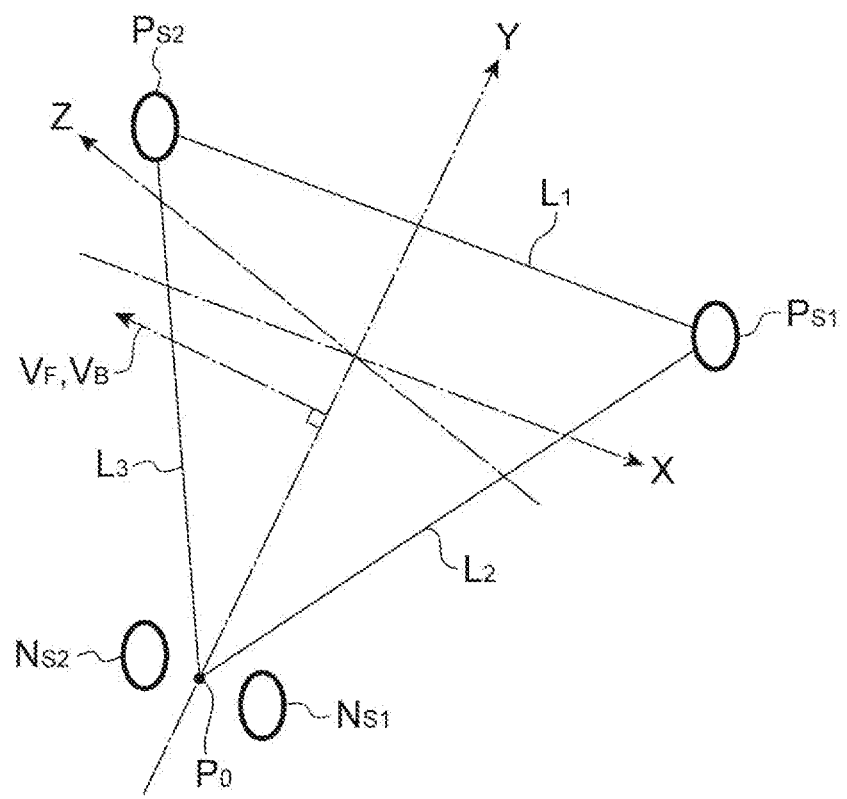
FIG. 16 is a diagram illustrating feature points.

First, a basic principle of the face detection method will be described. As illustrated in FIG. 16, the face posture of the subject M is indicated by a face posture vector $V_B$. The face posture vector $V_B$ is obtained using the pupils and nostrils of the subject M. For example, the face posture vector $V_B$ is a normal vector of a plane passing through three points of a position $P_{S1}$ of the left pupil center, a position $P_{S2}$ of the right pupil center, and a position $P_0$ of the center between the nostrils. The left pupil, the right pupil, the left nostril (first nostril) center, the right nostril (second nostril) center, and the center between the nostrils can be defined as feature points. Three-dimensional coordinates of these feature points can be obtained using several calculation schemes.

Figure 17:
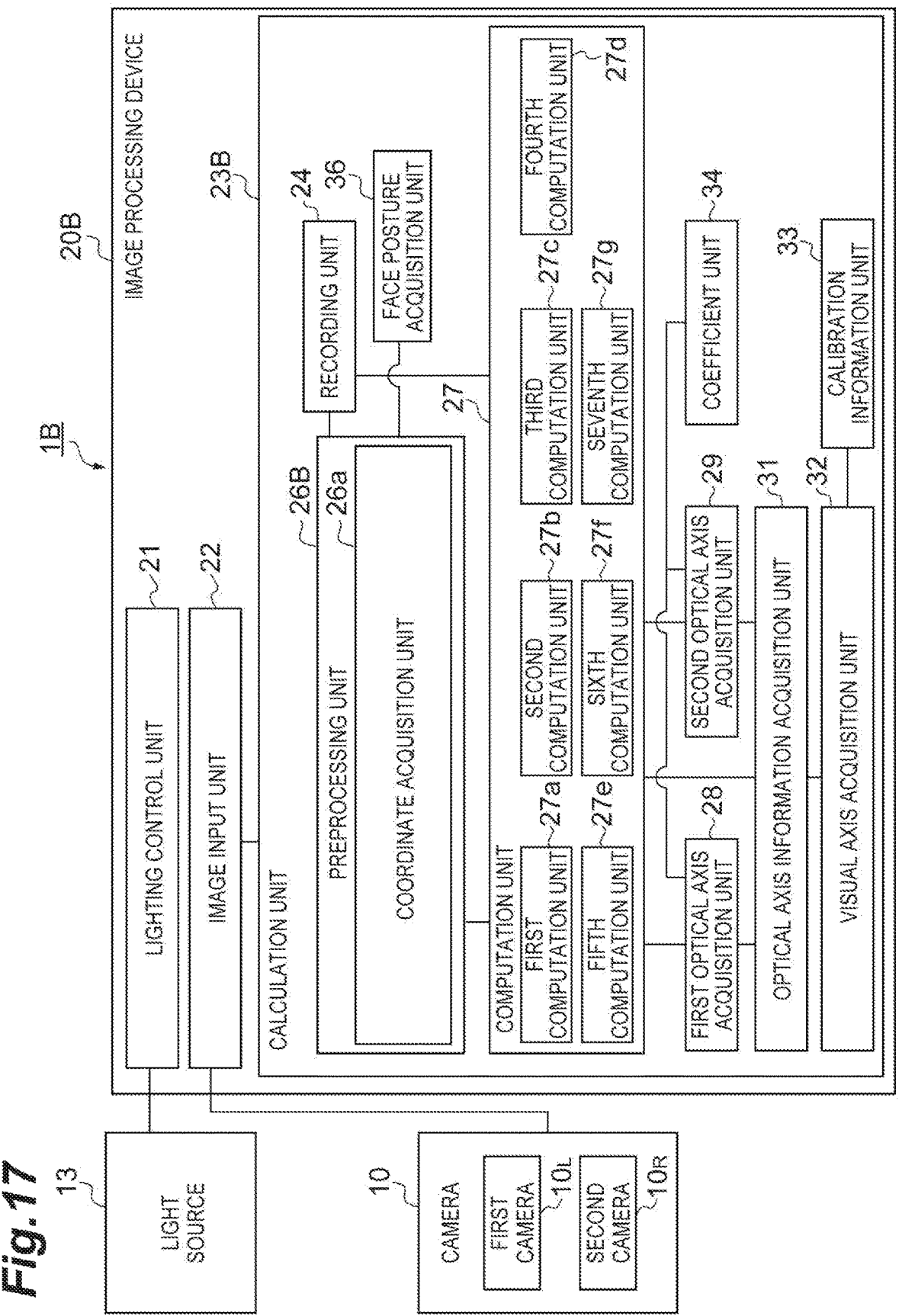
FIG. 17 is a functional block diagram illustrating a line-of-sight detection device according to another modification example.

As illustrated in FIG. 17, the line-of-sight detection device 1B physically has the same configuration as the line-of-sight detection device 1 according to the embodiment. On the other hand, in the line-of-sight detection device 1B, functional components in the image processing device 20B are different from those in the line-of-sight detection device 1. The line-of-sight detection device 1B includes a coordinate acquisition unit 26*a* and a face posture acquisition unit 36 as functional components for detecting a face posture. The coordinate acquisition unit 26*a* is included in the preprocessing unit 26B in the calculation unit 23B. The face posture acquisition unit 36 is included in the calculation unit 23B.

The coordinate acquisition unit 26*a* is a component of the preprocessing unit 26. The coordinate acquisition unit 26*a* obtains three-dimensional coordinates regarding the positions ($P_{S1}$, $P_{S2}$) of the pupil center. Further, the coordinate acquisition unit 26*a* obtains three-dimensional coordinates regarding the positions ($P_0$, $N_{S1}$, $N_{S2}$) of the nostrils. It should be noted that the coordinate acquisition unit 26*a* only has to be able to obtain the three-dimensional coordinates. Therefore, the coordinate acquisition unit 26*a* does not have to be a component of the preprocessing unit 26. Using the first image acquired by the first camera $10_L$ and the second image acquired by the second camera $10_R$, the coordinate acquisition unit 26*a* obtains three-dimensional coordinates of the position ($P_S1$, $P_{S2}$) of the pupil center and three-dimensional coordinates of the positions ($P_0$, $N_{S1}$, $N_{S2}$) of the nostrils using the stereo matching method.

Figure 18:
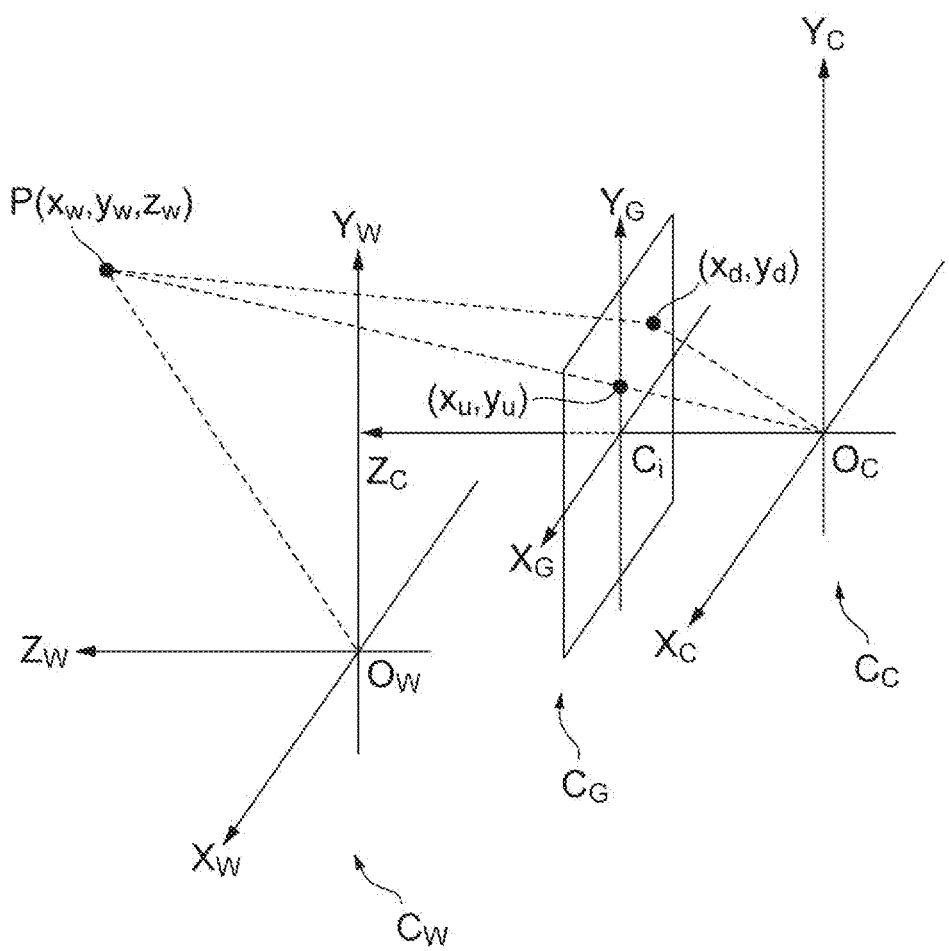
FIG. 18 is a diagram illustrating a relationship between a world coordinate system and a camera coordinate system.

Specifically, the coordinate acquisition unit 26*a* performs the following operation. As illustrated in FIG. 18, three coordinate systems are used for a determination of the three-dimensional coordinates of the pupil center using the stereo method. The three coordinate systems are a world coordinate system $C_W$ ($X_W$, $Y_W$, $Z_W$), a camera coordinate system $C_C$ ($X_C$, $Y_C$, $Z_C$), and an image coordinate system $C_G$ ($X_G$, $Y_G$, $Z_G$). The world coordinate system $C_W$ defines any point to be shared among a plurality of cameras. The three-dimensional coordinates of the feature point are based on the world coordinate system $C_W$. A relationship between the world coordinate system $C_W$ and the camera coordinate system $C_C$ is shown by Equation (28). A rotation matrix $M_R$ and a translation vector $T_R$ in Equation (28) are constants that are obtained through camera calibration. The coordinate acquisition unit 26*a* obtains the position ($P_{S1}$, $P_{S2}$) of the pupil center in the world coordinate system $C_W$ using Equation (28).

[Math. 28]

$$\begin{pmatrix} X_C \\ Y_C \\ Z_C \end{pmatrix} = M_R \begin{pmatrix} X_W \\ Y_W \\ Z_W \end{pmatrix} + T_R \qquad (28)$$

The face posture acquisition unit 36 obtains a face posture vector using the three-dimensional coordinates of the position ($P_{S1}$, $P_{S2}$) of the pupil center and three-dimensional coordinates of the positions ($N_{S1}$, $N_{S2}$) of the nostrils.

The face posture acquisition unit 36 obtains three reference parts using four pieces of coordinate information ($P_{S1}$, $P_{S2}$, $N_{S1}$, $N_{S2}$). A set of three reference parts is a reference part group. Then, the face posture acquisition unit 36 sets a virtual plane. The virtual plane is a triangular plane of which a vertex is a point indicated by the three generated reference parts. The face posture acquisition unit 36 obtains a face posture vector $V_B$ passing through a centroid of the virtual plane. The face posture vector $V_B$ is information indicating the face posture.

For example, the face posture acquisition unit 36 may select the position $P_{S1}$ of the pupil center of the right eye, the position $P_{S2}$ of the pupil center of the left eye, and the position $P_0$ of the center of the nostrils as the reference part group (see FIG. 16). The position $P_0$ of the center between the nostrils is an average of the position $N_{S1}$ of the right nostril and the position $N_{S2}$ of the left nostril. The face posture acquisition unit 36 selects the position $P_{S1}$ of the pupil center of the right eye, the position $P_{S2}$ of the pupil center of the left eye, and the position $N_{S1}$ of the right nostril as the first reference part group. The face posture acquisition unit 36 obtains a first normal vector using these. In addition, the face posture acquisition unit 36 selects the position $P_{S1}$ of the pupil center of the right eye, the position $P_{S2}$ of the pupil center of the left eye, and the position $N_{S2}$ of the left nostril as a second reference part group. The face posture acquisition unit 36 obtains a second normal vector using these. It should be noted that the face posture acquisition unit 36 may obtain an average of the first normal vector and the second normal vector as the face posture vector $V_B$.

The line-of-sight detection device 1B according to the modification example can extend the range in which the line of sight can be detected. Further, the line-of-sight detection device 1B can obtain a face posture of the subject M.

Modification Example 5

Figure 19:
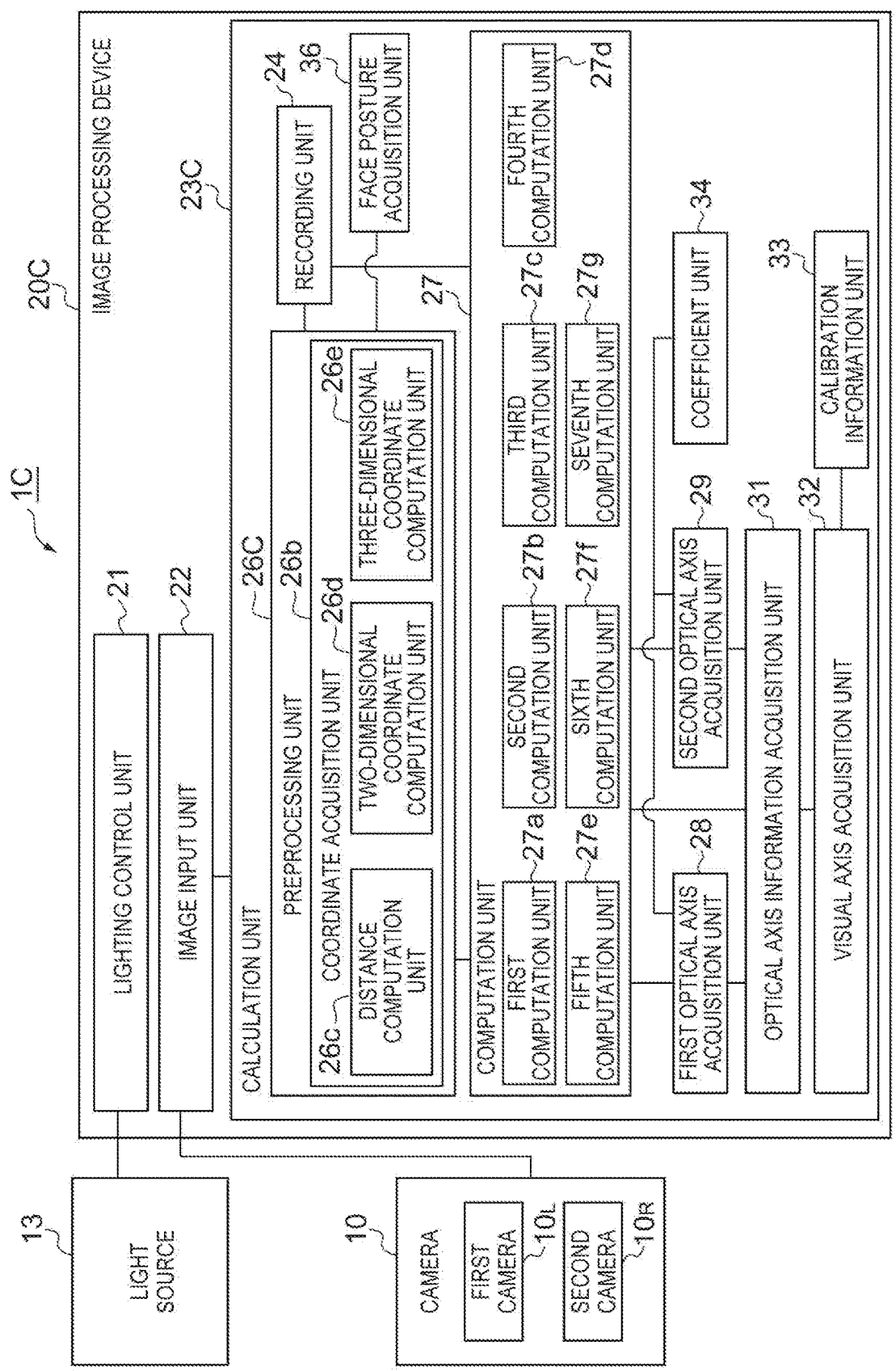
FIG. 19 is a functional block diagram illustrating a line-of-sight detection device according to still another modification example.

The operation of the coordinate acquisition unit is not limited to the process based on the stereo matching method. For an operation of the coordinate acquisition unit, any process may be selected as long as the process is a process capable of acquiring the three-dimensional coordinates of the pupil P and nostrils. For example, as illustrated in FIG. 19, the coordinate acquisition unit 26*b* may obtain three-dimensional coordinates through a process called a constraint condition method. In the constraint condition method, three-dimensional coordinates of feature points are obtained by using a distance between the feature points (hereinafter referred to as "inter-feature point distance" or simply a "distance") as constraint conditions. The inter-feature point distance is, for example, a distance $L_1$ between the position $P_{S1}$ of the left pupil center and the position $P_{S2}$ of the right pupil center, a distance $L_2$ between the position $P_{S1}$ of the left pupil center and the position $P_0$ of the center between the nostrils, and a distance $L_3$ between the position $P_{S2}$ of the right pupil center and the position $P_0$ of the center between the nostrils (see FIG. 16). Further, two optical systems (for example, cameras) are required to implement the stereo method. However, in the constraint condition method, three-dimensional coordinates can be obtained only with a third image acquired by one camera (a third camera). Therefore, according to the constraint condition method, it is possible to extend the detection range of the face direction in a separation direction of the optical system by disposing the two optical systems at a distance and using the respective optical systems.

As illustrated in FIG. 19, the line-of-sight detection device 1C physically has the same configuration as the line-of-sight detection device 1 according to the embodiment. On the other hand, in the line-of-sight detection device 1C, the functional components in the image processing device 20C are different from the line-of-sight detection device 1. The line-of-sight detection device 1C has a coordinate acquisition unit 26*b* as a functional component for detecting the face posture. The coordinate acquisition unit 26*b* is included in the preprocessing unit 26C in the calculation unit 23C. The coordinate acquisition unit 26*b* includes a distance computation unit 26*c*, a two-dimensional coordinate computation unit 26*d*, and a three-dimensional coordinate computation unit 26*e*. Further, the calculation unit 23C includes a face posture acquisition unit 36.

Figure 20:
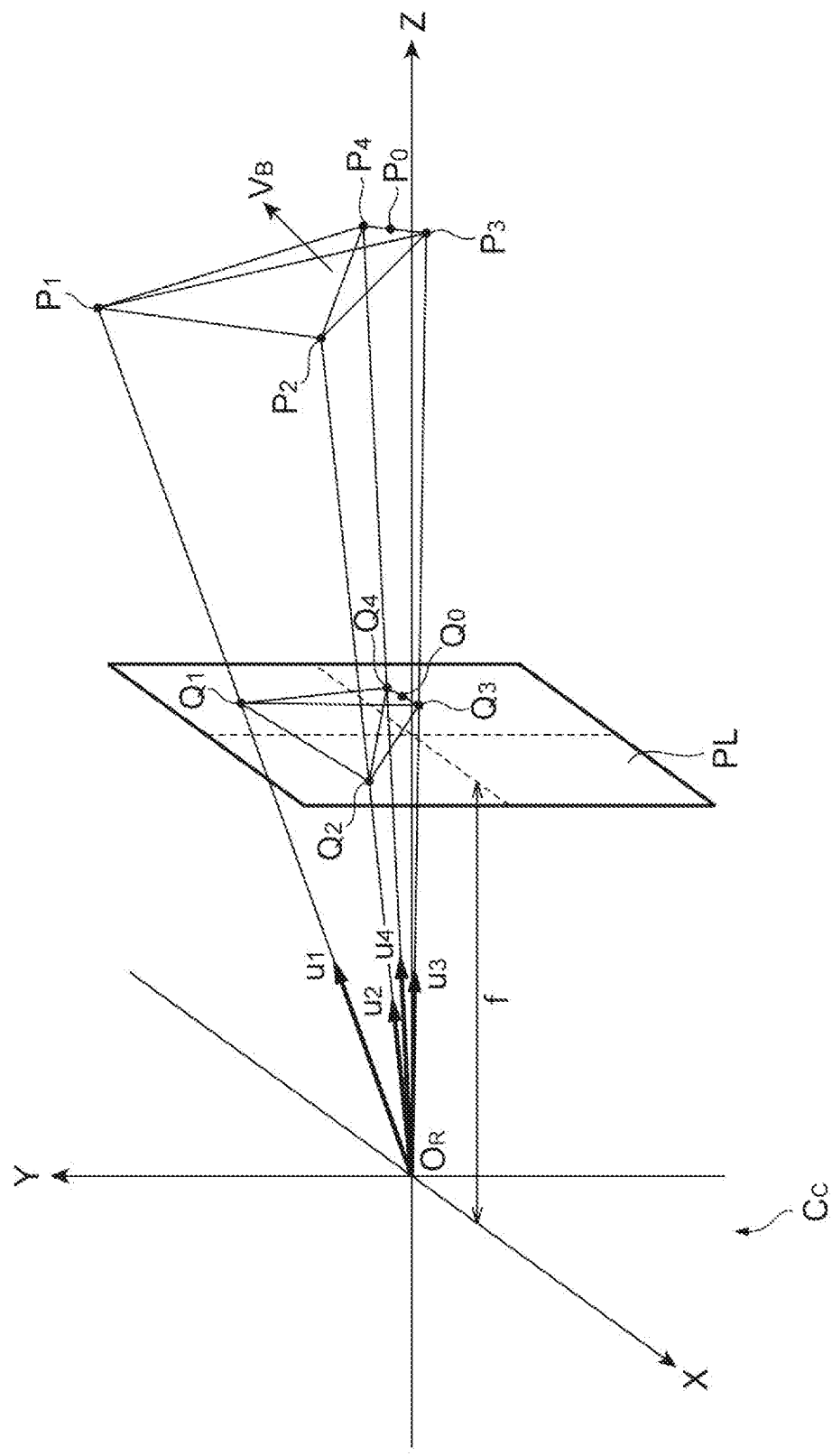
FIG. 20 is a diagram illustrating calculation of three-dimensional coordinates of feature points using a constraint condition method.

The imaging optical system in the line-of-sight detection device 1C can be assumed to be a pinhole model with a focal length f (see FIG. 20). Two-dimensional coordinates of center points of the right pupil, the left pupil, the left nostril, and the right nostril on a nostril image (imaging plane PL) in the camera coordinate system $C_C$ are $Q_1$, $Q_2$, $Q_3$, and $Q_4$. The camera coordinate system $C_C$ is assumed to be a position origin $O_R$ of the pinhole. Using the two-dimensional coordinates of the four points, the preprocessing unit 26 obtains coordinates (inter-nostril center coordinates) $P_0$ of a midpoint of both nostrils (a center between the nostrils), the position $P_{S1}$ of the right pupil center, and the position $P_{S2}$ of the left pupil center. Here, $P_n = (X_n, Y_n, Z_n)$ (n=0, 1, 2).

A distance of each side of a triangle connecting the three feature points (the center between the nostrils, the left pupil, and the right pupil) is shown as a distance $L_{ij}$ between the points i and j (see Equation (29)) when any one of the points is i and the other points are j. This distance $L_{ij}$ is obtained through actual measurement that is performed in advance. A process of obtaining the distance Lij is executed by the distance computation unit 26*c*.

[Math. 29]

$$L_{ij} = \sqrt{(X_i - X_j)^2 + (Y_i - Y_j)^2 + (Z_i - Z_j)^2} \qquad (29)$$

The two-dimensional position on the imaging plane PL corresponding to each feature point is shown by using a position vector from the pinhole to each feature point and the focal length f of the camera (see Equation (29)). The process of obtaining the two-dimensional position on the imaging plane PL is executed by the two-dimensional coordinate computation unit 26*d*.

[Math. 30]

$$Q_n = (X_n \times (f/Z_n), Y_n(f/Z_n)) \tag{30}$$

Further, a unit vector corresponding to the position vector directed from the pinhole to each feature point is shown by Equation (30).

[Math. 31]

$$\vec{u}_n = \frac{(x_n, y_n, f)}{\sqrt{x_n^2 + y_n^2 + f^2}} \tag{31}$$

The position vector of each feature point is shown by Equation (31) using the constant $a_n$ (n=0, 1, 2).

[Math. 32]

$$\vec{P} = a_n \vec{u}_n \tag{32}$$

Then, Equation (33) is established.

[Math. 33]

$$|P_m - P_n|^2 = a_m^2 + a_n^2 - 2 a_m a_n (\vec{u}_m, \vec{u}_n) = L_{mn}^2 \tag{33}$$

Accordingly, Equation (34) is obtained.

[Math. 34]

$$\begin{cases} a_0^2 + a_1^2 - 2a_0 a_1 (\vec{u}_0, \vec{u}_1) = L_{01}^2 \\ a_1^2 + a_2^2 - 2a_1 a_2 (\vec{u}_1, \vec{u}_2) = L_{12}^2 \\ a_2^2 + a_0^2 - 2a_2 a_0 (\vec{u}_2, \vec{u}_0) = L_{20}^2 \end{cases} \tag{34}$$

The face posture acquisition unit 36 obtains $a_0$, $a_1$, and $a_2$ using a simultaneous Equation (Equation (34)). The face posture acquisition unit 36 applies a solution to the simultaneous equation to Equation (32). As a result, the face posture acquisition unit 36 obtains a position vector. The position vector indicates three-dimensional coordinates of each feature point. The process of obtaining the three-dimensional coordinates is executed by the three-dimensional coordinate computation unit 26*e*.

The line-of-sight detection device 1C according to the modification example can extend the range in which the line of sight can be detected. Further, the line-of-sight detection device 1C can obtain a face posture of the subject M.

In the above embodiment, the information generated by the optical axis information acquisition unit 31 is information for selecting one of the first optical axis candidate and the second optical axis candidate as the optical axis AL. For example, the information generated by the optical axis information acquisition unit 31 may be information for generating the optical axis AL using both the first optical axis candidate and the second optical axis candidate (Equation (35)). In Equation (35), a weighting factor w1 is set in the information (magnitude $|\theta_1|$) of the first optical axis candidate, and a weighting factor w2 is set in information (magnitude $|\theta_2|$) of the second optical axis candidate. Therefore, the information generated by the optical axis information acquisition unit 31 may be the information indicating Equation (35) and the weighting factors w1 and w2 in Equation (35).

[Math. 35]

$$|\theta| = w1 \times |\theta_1| + w2 \times |\theta_2|$$

$$w1 + w2 = 1 \tag{35}$$

Figure 21:
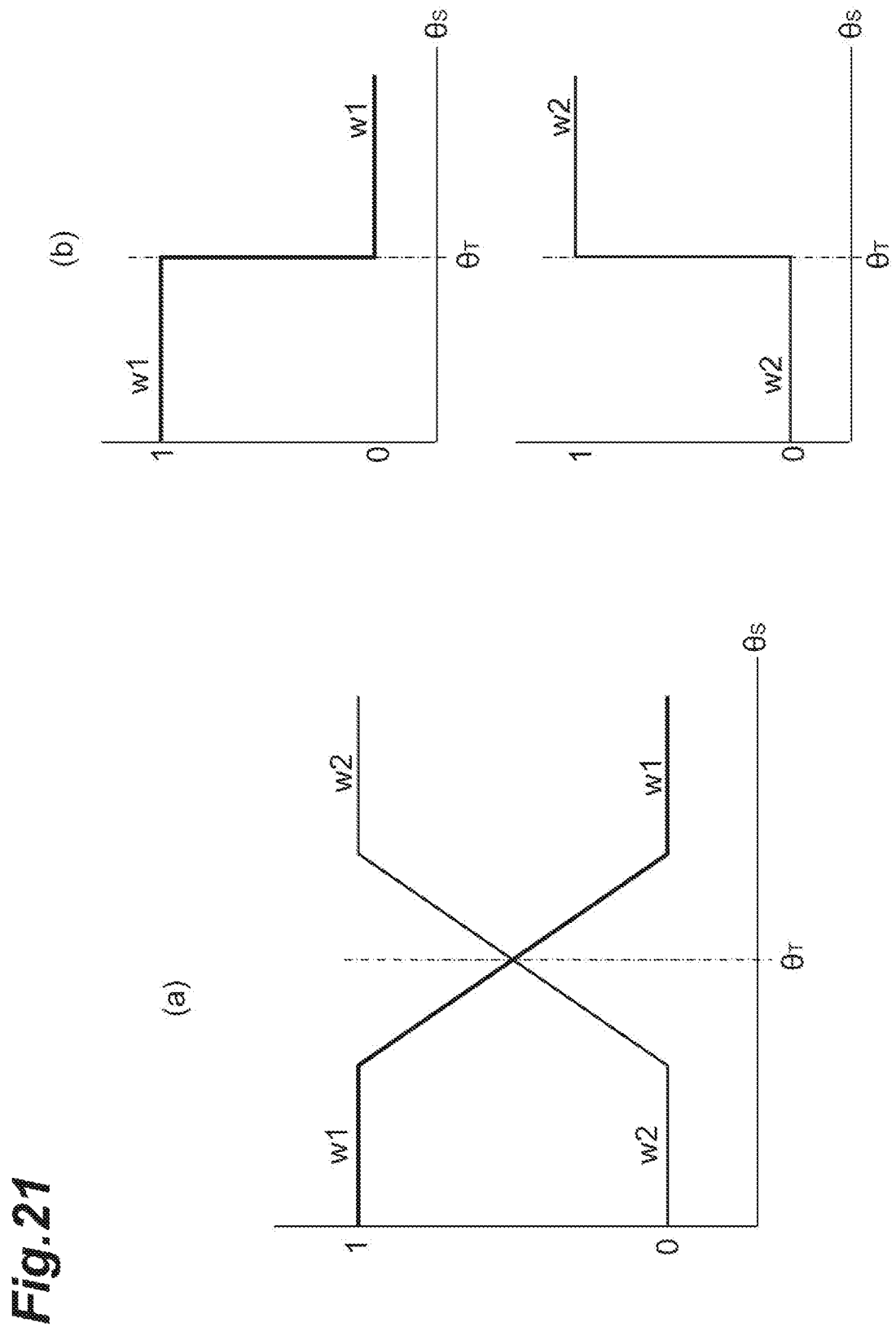
FIG. 21 is a diagram illustrating an operation of an optical axis information acquisition unit.

As illustrated in FIGS. 21(*a*) and 21(*b*), the weighting factors w1 and w2 can have values between 0 and 1 with the slope $\theta_S$ as a variable. As illustrated in FIG. 21(*a*), a threshold value $\theta_T$ (for example, 30 degrees) is set and a predetermined numerical range including the threshold value $\theta_T$ is set. In a case in which the slope $\theta_S$ does not exist within the predetermined numerical range and the slope $\theta_S$ exists on the side smaller than the predetermined numerical range, the weighting factor w1 is set to 1 and the weighting factor w2 is set to 0. On the other hand, when the slope $\theta_S$ does not exist within the predetermined numerical range and the slope $\theta_S$ exists on the side greater than the predetermined numerical range, the weighting factor w1 is set to 0 and the weighting factor w2 is set to 1. In other words, when the slope $\theta_S$ exists on the side smaller than the predetermined numerical range, the first optical axis candidate is set as the optical axis AL. On the other hand, when the slope $\theta_S$ exists on the side greater than the predetermined numerical range, the second optical axis candidate is set as the optical axis AL. Further, when the slope $\theta_S$ is within the predetermined numerical range, the optical axis AL may be obtained using the weighting factor w1 and the weighting factor w2. For example, when the slope $\theta_S$ is equal to the threshold value $\theta_T$, the weighting factor w1 may be set to 0.5 and the weighting factor w2 may be set to 0.5. Further, as illustrated in FIG. 21(*b*), a relationship between the weighting factors w1 and w2 and the slope $\theta_S$ may be changed stepwise. In this case, when the slope $\theta_S$ is smaller than the threshold value $\theta_T$, the first optical axis candidate is used for acquisition of the optical axis AL. When the slope $\theta_S$ is greater than the threshold value $\theta_T$, the second optical axis candidate is used for acquisition of the optical axis AL. That is, this is the same as the operation of the optical axis information acquisition unit 31 shown in the above embodiment.

REFERENCE SIGNS LIST

1 Line-of-sight detection device
10, 10$_L$, 10$_R$ Camera (image acquisition unit)
11 Objective lens
12 Opening
13 Light source
13*a*, 13*b* Light emitting element
15 Optical system
20 Image processing device (Image processing unit)
21 Lighting control unit
22 Image input unit
23 Calculation unit
24 Recording unit
26 Preprocessing unit
27 Computation unit
27*a* First computation unit
27*b* Second computation unit
27*c* Third computation unit
27*d* Fourth computation unit
27*e* Fifth computation unit 27f Sixth computation unit
28 First optical axis acquisition unit
29 Second optical axis acquisition unit
30 Display device
31 Optical axis information acquisition unit
32 visual axis acquisition unit
33 Calibration information unit
34 Coefficient unit
35 Direction determination unit
50 Eyeball
52 Cornea
53 Crystalline lens
56 Retina
57 Fovea centralis
101 CPU
102 Main storage device
103 Auxiliary storage device
104 Communication control unit
105 Input device
106 Output device
A1, A2 Visual target
A3 Axis line
AL Optical axis
AS Visual line
CL Intersection line
G Corneal reflection
OP Camera-pupil center vector
P, Pa, Pb, Pc pupil
PQ, PT Line-of-sight vector
Q, T Gazing point
r, $r_1$, $r_2$ Corneal reflection-pupil center vector
M Subject
VS Virtual viewpoint plane
$VL_1$, $VL_2$ Virtual optical axis plane.

The invention claimed is:

1. A line-of-sight detection device comprising:
an image acquisition unit that obtains a plurality of eye images including eyes of a subject;
a light source that is disposed near the image acquisition unit and irradiates the subject with light for causing corneal reflection in the eye; and
an image processing unit that acquires information on a pupil shape of the eye, a position ($P_S$) of a pupil center and a position ($G_S$) of corneal reflection included in the plurality of eye images using the plurality of eye images, and obtains a line of sight of the subject based on the acquired information,
wherein the image processing unit includes
a first optical axis acquisition unit that acquires a first optical axis candidate using the position ($P_S$) of the pupil center and the position ($G_S$) of the corneal reflection;
a second optical axis acquisition unit that acquires a second optical axis candidate by using the pupil shape;
a computation unit that approximates an outer shape of the pupil included in the plurality of eye images as a predetermined shape and obtains an evaluation value ($R=L_A/L_B$) indicated by a major diameter ($L_A$) and a minor diameter ($L_B$) of the predetermined shape;
an optical axis information acquisition unit that generates information for acquiring an optical axis using the evaluation value based on the pupil shape and outputs as an optical axis one of the first optical axis candidate and the second optical axis candidate selected on the basis of the generated information;
a calibration information unit that provides calibration information indicating a deviation of the optical axis with respect to a visual axis of the eye; and
a visual axis acquisition unit that obtains the visual axis as the line of sight by calibrating the optical axis using the calibration information, and
wherein the optical axis information acquisition unit
generates information to select the first optical axis candidate as the optical axis if a slope $\theta_S$ obtained as an inverse cosine component of a reciprocal of the evaluation value ($R=L_A/L_B$) is smaller than a threshold value, and
generates information to select the second optical axis candidate as the optical axis if the slope $\theta_S$ obtained as the inverse cosine component of the reciprocal of the evaluation value ($R=L_A/L_B$) is greater than the threshold value.

2. The line-of-sight detection device according to claim 1, wherein the calibration information is a deviation angle ($\theta_0$), and
the deviation angle ($\theta_0$) is a vector indicating a deviation of the optical axis with respect to the visual axis, and is indicated by a magnitude ($|\theta_0|$) and a slope ($\phi_0$) of the optical axis with respect to the visual axis.

3. The line-of-sight detection device according to claim 1, wherein the image processing unit includes
a first computation unit that obtains a first vector (OP) directed from a position ($O_S$) of the image acquisition unit to the position ($P_S$) of the pupil center;
a second computation unit that obtains a second vector (r) directed from the position ($G_S$) of the corneal reflection to the position ($P_S$) of the pupil center;
a third computation unit that obtains a virtual viewpoint plane having the first vector ($O_P$) as a normal;
a fourth computation unit that approximates an outer shape of the pupil included in the plurality of eye images as an ellipse and obtains an ellipticity ($R=L_A/L_B$) indicated by a major diameter ($L_A$) and a minor diameter ($L_B$) of the ellipse; and
a fifth computation unit that obtains a slope ($\gamma'$) between a minor axis of the ellipse and a horizontal axis,
the first optical axis acquisition unit acquires the first optical axis candidate indicated by a magnitude ($|\theta|$) of an angle ($\theta$) with reference to the first vector (OP) and a slope ($\phi$) with reference to a horizontal axis included in the virtual viewpoint plane using a magnitude ($|r|$) of the second vector (r) associated with the magnitude ($|\theta|$) of the angle ($\theta$) and a slope ($\phi'$) formed by the second vector (r) associated with the slope ($\phi$) and the horizontal axis, and
the second optical axis acquisition unit obtains the second optical axis candidate indicated by the magnitude ($|\theta|$) of the angle ($\theta$) with reference to the first vector (OP) and the slope ($\phi$) with reference to the horizontal axis included in the virtual viewpoint plane using the ellipticity (R) associated with the magnitude ($|\theta|$) of the angle ($\theta$) and the slope ($\gamma'$) associated with the slope ($\phi$).

4. The line-of-sight detection device according to claim 3, wherein the first optical axis acquisition unit associates the magnitude ($|r|$) of the second vector (r) with the magnitude ($|\theta|$) of the angle ($\theta$) using a first coefficient (k).

5. The line-of-sight detection device according to claim 4, wherein the image acquisition unit includes a first camera that obtains a first eye image included in the plurality of eye images and that is disposed at a first camera position ($O_{S1}$), and a second camera that obtains a second eye image included in the plurality of eye images and that is disposed at a second camera position ($O_{S2}$), the eye includes a first eye and a second eye, the first eye includes a position ($G_{S1}$) of first corneal reflection, a position ($P_{S1}$) of a first pupil center, and a first optical axis, the second eye includes a position ($G_{S2}$) of second corneal reflection, a position ($P_{S2}$) of a second pupil center, and a second optical axis, the image processing unit further includes a sixth computation unit that obtains information on a first virtual optical axis plane including the first camera position ($O_{S1}$), the position ($P_{S1}$) of the first pupil center, and a position at which the first optical axis intersects a first virtual viewpoint plane having a fourth vector as a normal on the basis of a third vector ($r_1$) directed from the position ($G_{S1}$) of the first corneal reflection to the position ($P_{S1}$) of the first pupil center and the fourth vector from the first camera position ($O_{S1}$) to the position ($P_{S1}$) of the first pupil center using the first eye image;

a seventh computation unit that obtains information on a second virtual optical axis plane including the second camera position ($O_{S2}$), the position ($P_{S2}$) of the second pupil center, and a position at which the second optical axis intersects a second virtual viewpoint plane having a sixth vector as a normal on the basis of a fifth vector ($r_2$) directed from the position ($G_{S2}$) of the second corneal reflection to the position ($P_{S2}$) of the second pupil center and the sixth vector from the second camera position ($O_{S2}$) to the position ($P_{S2}$) of the second pupil center using the second eye image; and a coefficient unit that obtains the first coefficient (k), and the coefficient unit obtains the first coefficient ($k_1$) corresponding to the first eye using a fifth angle ($\theta_1$) obtained from an intersection line at which the first virtual optical axis plane and the second virtual optical axis plane intersect each other and a magnitude ($|r_1|$) of the third vector ($r_1$), and obtains the first coefficient ($k_2$) corresponding to the second eye using a fifth angle ($\theta_2$) obtained from the intersection line and the sixth vector, and a magnitude ($|r_2|$) of the fifth vector ($r_2$).

6. The line-of-sight detection device according to claim 5, wherein the fourth computation unit obtains a first ellipse ($R_1 = L_{A1}/L_{B1}$) that is a ratio of a major diameter ($L_{A1}$) to a minor diameter ($L_{B1}$) of the ellipse indicating an outer shape of the pupil included in the first eye image using the first eye image, and acquires a second ellipse ($R2 = L_{A2}/L_{B2}$) which is a ratio of a major diameter ($L_{A2}$) to a minor diameter ($L_{B2}$) of the ellipse indicating an outer shape of the pupil included in the second eye image using the second eye image, and the image processing unit further includes a direction determination unit that compares the first ellipse ($R_1$) with the second ellipse ($R_2$) to distinguish a line-of-sight direction of the subject in a horizontal direction.

7. The line-of-sight detection device according to claim 3, wherein the second optical axis acquisition unit associates an inverse cosine component of a reciprocal of the ellipticity (R) with the magnitude ($|\theta|$) of the angle ($\theta$) using a second coefficient (h).

8. The line-of-sight detection device according to claim 3, wherein the second optical axis acquisition unit uses a corrected ellipticity (R') obtained by correcting the deviation of a pupil contour caused by refraction of a cornea of an eyeball of the subject in acquisition of the magnitude ($|\theta|$) of the angle ($\theta$).

9. The line-of-sight detection device according to claim 1, wherein the eye includes a first eye and a second eye, and the image processing unit further includes a coordinate acquisition unit that acquires respective three-dimensional coordinates of a position ($P_{S1}$) of the pupil center in the first eye, a position ($P_{S2}$) of the pupil center in the second eye, a position ($N_{S1}$) of a first nostril among a pair of nostrils of the subject, and a position ($N_{S2}$) of a second nostril among the pair of nostrils of the subject; and a face posture acquisition unit that acquires a face posture of the subject using the position ($P_{S1}$) of the pupil center, the position ($P_{S2}$) of the pupil center, the position ($N_{S1}$) of the first nostril, and the position ($N_{S2}$) of the second nostril.

10. The line-of-sight detection device according to claim 9, wherein the image acquisition unit include a first camera that obtains a first image including a face of the subject, and a second camera that is disposed at a position separated from the first camera and obtains a second image including the face of the subject, and the coordinate acquisition unit acquires the respective three-dimensional coordinates of the position ($P_{S1}$) of the pupil center in the first eye, the position ($P_{S2}$) of the pupil center in the second eye, the position ($N_{S1}$) of the first nostril, and the position ($N_{S2}$) of the second nostril using a stereo matching method based on the first image and the second image.

11. The line-of-sight detection device according to claim 10, wherein the image acquisition unit includes one third camera that obtains a third image including a face of the subject, and the coordinate acquisition unit includes a distance computation unit that calculates a distance between three feature points generated from the first eye, the second eye, the first nostril, and the second nostril;

a two-dimensional coordinate computation unit that calculates two-dimensional coordinates of three feature points in the third image using the third image acquired by the third camera; and a three-dimensional coordinate computation unit that calculates three-dimensional coordinates of each of the three generated feature points using the distance acquired by the distance computation unit and the two-dimensional coordinates acquired by the coordinate acquisition unit.

12. The line-of-sight detection device according to claim 1, wherein the optical axis information acquisition unit generates information for selecting one of the first optical axis candidate and the second optical axis candidate as the optical axis on the basis of the pupil shape.

13. A line-of-sight detection device comprising:

an image acquisition unit that obtains a plurality of eye images including eyes of a subject;

a light source that is disposed near the image acquisition unit and irradiates the subject with light for causing corneal reflection in the eye; and an image processing unit that acquires information on a pupil shape of the eye, a position ($P_S$) of a pupil center and a position ($G_S$) of corneal reflection included in the plurality of eye images using the plurality of eye images, and obtains a line of sight of the subject based on the acquired information, wherein the image processing unit includes a first optical axis acquisition unit that acquires a first optical axis candidate using the position ($P_S$) of the pupil center and the position ($G_S$) of the corneal reflection;

a second optical axis acquisition unit that acquires a second optical axis candidate on the basis of the pupil shape by using an evaluation value ($R'$) obtained by correcting a deviation of a pupil contour caused by refraction of a cornea of the eye of the subject;

a computation unit that approximates an outer shape of the pupil included in the plurality of eye images as a predetermined shape and obtains an evaluation value ($R=LA/LB$) indicated by a major diameter (LA) and a minor diameter (LB) of the predetermined shape;

an optical axis information acquisition unit that generates information for acquiring an optical axis using the evaluation value based on the pupil shape and outputs as an optical axis at least one of the first optical axis candidate and the second optical axis candidate on the basis of the pupil shape;

a calibration information unit that provides calibration information indicating a deviation of the optical axis with respect to a visual axis of the eye; and a visual axis acquisition unit that obtains the visual axis as the line of sight by calibrating the optical axis using the calibration information.

* * * * *